US008722036B2

(12) United States Patent
Shafren

(10) Patent No.: US 8,722,036 B2
(45) Date of Patent: *May 13, 2014

(54) METHODS FOR TREATING MALIGNANCIES USING COXSACKIEVIRUSES

(75) Inventor: Darren R. Shafren, New Lambton (AU)

(73) Assignee: Viralytics Limited, Pymble (AU)

( * ) Notice: Subject to any disclaimer, the term of this patent is extended or adjusted under 35 U.S.C. 154(b) by 307 days.

This patent is subject to a terminal disclaimer.

(21) Appl. No.: 12/040,813

(22) Filed: Feb. 29, 2008

(65) Prior Publication Data

US 2009/0123427 A1    May 14, 2009

Related U.S. Application Data

(62) Division of application No. 10/148,008, filed as application No. PCT/AU00/01461 on Nov. 27, 2000, now Pat. No. 7,361,354.

(30) Foreign Application Priority Data

Nov. 25, 1999 (AU) ...................................... PQ4256

(51) Int. Cl.
*A01N 63/00* (2006.01)
*A61K 39/125* (2006.01)
*A61P 35/00* (2006.01)

(52) U.S. Cl.
USPC .................... 424/93.6; 424/204.1; 424/216.1; 435/235.1; 514/19.3

(58) Field of Classification Search
None
See application file for complete search history.

(56) References Cited

U.S. PATENT DOCUMENTS

| | | | | |
|---|---|---|---|---|
| 5,529,774 | A | 6/1996 | Barba et al. ................ | 424/93.21 |
| 5,585,096 | A | 12/1996 | Martuza et al. ............. | 424/93.2 |
| 5,585,254 | A | 12/1996 | Maxwell et al. ............. | 435/465 |
| 5,601,818 | A | 2/1997 | Freeman et al. ........... | 424/93.21 |
| 5,674,729 | A | 10/1997 | Wimmer et al. ........... | 435/235.1 |
| 5,681,731 | A | 10/1997 | Lebkowski et al. ........... | 435/457 |
| 5,688,773 | A | 11/1997 | Chiocca et al. ................ | 514/44 |
| 5,714,374 | A * | 2/1998 | Arnold et al. .............. | 435/235.1 |
| 5,972,706 | A | 10/1999 | McCormick .................. | 435/440 |
| 6,060,316 | A | 5/2000 | Young et al. .................. | 435/455 |
| 6,110,461 | A | 8/2000 | Lee et al. ..................... | 424/93.6 |
| 6,136,307 | A | 10/2000 | Lee et al. ..................... | 424/93.6 |
| 6,261,555 | B1 | 7/2001 | Lee et al. ..................... | 424/93.6 |
| 6,264,940 | B1 * | 7/2001 | Gromeier et al. ............ | 424/93.2 |

FOREIGN PATENT DOCUMENTS

| | | |
|---|---|---|
| AU | 1994699487 | 11/1994 |
| AU | 1996699811 | 12/1996 |
| AU | 1998726500 | 9/1998 |
| AU | 2001776401 | 9/2000 |
| AU | 2001782402 | 4/2001 |
| AU | 2001776061 | 5/2001 |
| AU | 2001782020 | 5/2001 |
| AU | 2001770517 | 6/2001 |
| AU | 2001/784776 | 10/2001 |
| AU | 2003258060 | 10/2003 |
| AU | 2004202292 | 6/2004 |
| AU | 2004203458 | 8/2004 |
| AU | 2005201079 | 4/2005 |
| CA | 2 051 289 | 3/1992 |
| EP | 1032269 | 9/2000 |
| WO | WO 90/12087 | 10/1990 |
| WO | WO 93/09221 | 5/1993 |
| WO | WO 94/18992 | 9/1994 |
| WO | WO 96/00007 | 1/1996 |
| WO | WO 97/23577 | 7/1997 |
| WO | WO 00/50618 | 2/1999 |
| WO | WO 99/18799 | 4/1999 |
| WO | WO 99/18992 | 4/1999 |
| WO | WO 99/28750 | 6/1999 |
| WO | WO 99/45783 | 9/1999 |
| WO | WO 00/08166 | 2/2000 |
| WO | WO 00/62735 | 10/2000 |
| WO | WO 01/04334 | 1/2001 |
| WO | WO 01/12815 | 2/2001 |
| WO | WO 01/19380 | 3/2001 |
| WO | WO 01/53506 | 7/2001 |
| WO | WO 02/43647 | 6/2002 |
| WO | WO 02/50304 | 6/2002 |
| WO | WO 02/087625 | 11/2002 |
| WO | WO 02/091997 | 11/2002 |
| WO | WO 02/092826 | 11/2002 |
| WO | WO 03/008586 | 1/2003 |
| WO | WO 03/010306 | 2/2003 |
| WO | WO 03/073918 | 9/2003 |
| WO | WO 03/082200 | 10/2003 |
| WO | WO 03/092579 | 11/2003 |
| WO | WO 03/094938 | 11/2003 |
| WO | WO 2004/003562 | 1/2004 |

(Continued)

OTHER PUBLICATIONS

Shafren et al (Clinical Cancer Research, 2004, 10:53-60, IDS).*
Skelding et al (Breast Cancer Res Treat, 2009, 113:21-30).*
Au et al (British J of Haematology, 2007, 137:133-141).*
Pulli et al (Virology, 1995, 212:30-38, IDS).*
Sachs et al (Urology, 2002, 60:531-536).*
Lang et al (J Clinical Investigations, 1965, 44:1125-1131).*
Suskind et al (Proc Soc Exp Biol Med, 1957, 94:309-318, IDS).*
Shafren et al (J of Virology, 1997, 71:9844-9848, IDS).*
Pasch et al (J of General Virology, 1999, 80:3153-3158).*
Fox et al (Breast Cancer research and Treatment, 1995, 36:219-226).*

(Continued)

*Primary Examiner* — Laura B Goddard
(74) *Attorney, Agent, or Firm* — DLA Piper LLP (US)

(57) ABSTRACT

There is a disclosed a method of killing abnormal cells such as malignant cells including melanoma cells, using a virus recognising at least one of a cell adhesion molecule and a complement regulatory protein. The virus may be a member of the Picornaviridae family. Coxsackie A-group viruses have been found to be particularly suitable. The cell adhesion molecule is desirably a member of the immunoglobulin (Ig) superfamily. Typically, the complement regulatory protein will be DAF.

10 Claims, 13 Drawing Sheets

(56) References Cited

FOREIGN PATENT DOCUMENTS

| WO | WO 2004/054613 | 7/2004 |
|----|----------------|--------|
| WO | WO 2005/002607 | 1/2005 |
| WO | WO 2005/007824 | 1/2005 |
| WO | WO 2005/030139 | 4/2005 |
| WO | WO 2005/087931 | 9/2005 |
| WO | WO 2005/107474 | 11/2005 |
| WO | WO 2006/002394 | 1/2006 |
| WO | WO 2006/047301 | 5/2006 |

OTHER PUBLICATIONS

Kelly et al (Am J Physiol Gastrointest Liver Physiol, 1992, 263:G864-G870).*
Giok et al (American Journal of Epidemiology, 1967, 85:93-100).*
Nastac et al (Neoplasma, 1963, 10:65-74).*
Coxsackievirus Material Safety Data Sheet of the Public Health Agency of Canada, printed 2010.*
Hyypia et al (Virus Research, 1993, 27:71-78).*
Alemany et al., "Gene Therapy for Gliomas: Molecular Targets, Adenoviral Vectors, and Oncolytic Adenoviruses", *Experimental Cell Research*, 252:1-12, Academic Press (1999).
Anastassiou et al., "Expression of VLA-2, VLA-3 and a.sub.v integrin receptors in ureal melanoma: association with microvascular architecture of the tumour and prognostic value", *Br. J. Ophthalmol.* 2000; 84:899-902.
Andreansky et al., "The Application of Genetically Engineered Herpes Simplex Viruses to the Treatment of Experimental Brain Tumors", *Proc. Natl. Acad. Sci.*, USA, 93:11313-11318 (1996).
Bacus et al., "Medullary Carcinoma is Associated with Expression of Intercellular Adhesion Molecule-1. Implication to its Morphology and its Clinical Behavior", *Am. J. Pathol.* 145(6):1337-48, Abstract (1994).
Berendt et al., "The Binding Site on ICAM-1 for Plasmodium Falciparum-Infected Erythrocytes Overlaps, but is Distinct from, the LFA-1-Binding Site", *Cell*, 68:71-81, Cell Press (1992).
Bjørge et al., "Characterization of the Complement-Regulatory Proteins Decay-Accelerating Factor (DAF,CD55) and Membrane Cofactor Protein (MCP, CD46) on a Human Colonic Adenocarcinoma Cell Line", *Cancer Immunol. Immunother.*, 42:185-192, Springer Verlag (1996).
Casasnovas & Springer, "Pathway of Rhinovirus disruption by soluble intercellular adhesion molecule-1 (ICAM-1): an intermediate in which ICAM-1 is bound and RNA is released", *Journal of Virology*, 68(9): 5882-5889 (1994).
Cheung et al., "Decay-Accelerating Factor Protects Human Tumor Cells from Complement-Mediated Cytotoxicity in Vitro", *J. Clin. Invest.*, 81:1122-1128, The American Society for Clinical Investigation, Inc. (1988).
Coffey et al., "Reovirus Therapy of Tumors with Activated Ras Pathway", *Science*, 282 (5392):1332-1334, Abstract, The American Association for the Advancement of Science (1998).
Colonno et al., "Isolation of a Monoclonal Antibody That Blocks Attachment of the Major Group of Human Rhinoviruses", *Journal of Virology*, 57(1):7-12, American Society for Microbiology (1986).
Darai et al "Soluble adhesion molecule in serum and cyst fluid from patients with cystic tumours of the ovary", *Human Reproduction*, 13:2831-2835 (1998).
Davies et al., "Comparison of Extracellular Matrix in Human Osteosarcomas and Melanomas Growing as Xenografts, Muticellular Spheroids, and Monolayer Cultures", *Anticancer Research*, 17:4317-4326 (1997).
DeTulleo & Kirchhausen, "The clathrin endocytic pathway in viral infection", *The EMBO Journal*, 17(16):4585-4593 (1998).
Fenner et al., "The Biology of Animal Viruses," Second ed., 20-22, 40, 348-392, *Academic Press*, New York and London (1974).
Fernandez-Real et al., "Expression of ICAM-1 in Distant Metastatic Thyroid Carcinoma", *J. Endocrinol. Invest.*, 19(3):183-185, Abstract (1996).
Fields et al., "Fields Virology," *Lippincott-Raven Publishers*, Philadelphia, Third ed., 25, 174-176, 499-500 (1996).

Fiucci et al "Caveolin-1 inhibits anchorage-independent growth, anoikis and invasiveness in MCF-7 human breast cancer cells", *Oncogene*, 21: 2365-2375 (2002).
Greve et al., "The Major Human Rhinovirus Receptor is ICAM-1", Cell, 56:839-847, Cell Press (1989).
Greve et al "Mechanisms of receptor-mediated Rhinovirus neutralization defined by two soluble forms of ICAM-1", Journal of Virology, 65(11):6015-6023 (1991).
Hemmi et al., "The Presence of Human Coxsackievirus and Adenovirus Receptor is Associated with Efficient Adenovirus-Mediated Transgene Expression in Human Melanoma Cell Cultures", *Human Gene Therapy*, 9:2363-2373, Mary Ann Liebert, Inc. (1998).
Hon Pui et al "Serum intercellular adhesion molecule-1 in childhood malignancy", *Blood*, 82(3):895-898 (1993).
Johnson et al., "De novo Expression of Intercellular-Adhesion Molecule 1 in Melanoma Correlates with Increased Risk of Metastasis", *Proc. Natl. Acad, Sci. USA*, 86:641-644 (1989).
Johnson et al., "The Melanoma Progression-Associated Antigen P3.58 is Identical to the Intercellular Adhesion Molecule, ICAM-1", *Immunobiol.*, 178:275-284 (1988).
Johnson, Judith P., "Cell Adhesion Molecules of the Immunoglobulin Supergene Family and their Role in Malignant Transformation and Progression to Metastatic Disease", *Cancer and Metastasis Reviews*, 10:11-22, Kluwer Academic Publishers (1991).
Kageshita et al., "Clinical Relevance of ICAM-1 Expression in Primary Lesions and Serum of Patients with Malignant Melanoma", *Cancer Research*, 53:4927-4932 (1993).
Kang, X. et al "Clinical evaluation of serum concentrations of intercellular adhesion molecule-1 in patients with colorectal cancer", *World Journal of Gastroenterology*, 11(27):4250-4253 (2005).
Karnauchow et al., "Short Consensus Repeat Domain 1 of Decay-Accelerating Factor is Required for Enterovirus 70 Binding", *Journal of Virology*, 72(11):9380-9383, American Society for Microbiology (1998).
Karnauchow et al., "The HeLa Cell Receptor for Enterovirus 70 Is Decay-Accelerating Factor (CD55)", *Journal of Virology*, 70(8):5143-5152, American Society for Microbiology (1996).
Koyama et al., "Expression of Intercellular Adhesion Molecule 1 (ICAM-1) During the Development of Invasion and/or Metastasis of Gastric Carcinoma", *J. Cancer Res. Clin. Oncol.*, 118(8):609-14, Abstract, Springer-Verlag (1992).
Kraus et al., "Analysis of the Expression of Intercellular Adhesion Molecule-1 and MUC18 on Benign and Malignant Melanocytic Lesions using Monoclonal Antibodies Directed Against Distinct Epitopes and Recognizing Denatured, Non-Glycosylated Antigen", *Melanoma Research*, 7 (Suppl. 2):S75-581, Rapid Science Publishers (1997).
Lea et al., "Determination of the Affinity and Kinetic Constants for the Interaction between the Human Virus Echovirus 11 and Its Cellular Receptor, CD55", *The Journal of Biological Chemistry*, 273 (46):30443-30447, The American Society for Biochemistry and Molecular Biology, Inc. (1998).
Lineberger et al, *J. of Virology*, 64:2582-2587 (1990).
Lonberg-Holm et al, "Unrelated animal viruses share receptors", *Nature*, 259:679-681 (1976).
Marjomaki et al "Internalization of Echovirus 1 in Caveolae", *Journal of Virology*, 1856-1865 (2002).
Marshall & Hart, "The Role of αv-Integrins in Tumour Progression and Metastasis", *Cancer Biology*, 7:129-138, Academic Press Ltd. (1996).
Martin et al "Efficient neutralization and disruption of Rhinovirus by chimeric ICAM-1/Immunoglobulin molecules", *Journal of Virology*, 67(6):3561-3568 (1993).
Miller & Welch, "Intercellular Adhesion Molecule-1 (ICAM-1) Expression by Human Melanoma Cells: Association with Leukocyte Aggregation and Metastatic Potential", Division of Chemotherapy, *Glaxo Research Laboratories*, Research Triangle Park, NC 27709 (Abstract).
Morandini et al., "Modulation of ICAM-1 Expression by α-MSH in Human Melanoma Cells and Melanocytes", *Journal of Cellular Physiology*, 175:276-282, Wiley-Liss, Inc. (1998).

(56) References Cited

OTHER PUBLICATIONS

Nasu et al "Serum levels of soluble intercellular adhesion molecule-1 (ICAM-1) and the expression of ICAM-1 mRNA in uterine cervical cancer", *Gynecol. Oncol.*, 65(2): 304-308 (1997).

Nasu et al., "Immunohistochemical Analysis of Intercellular Adhesion Molecule-1 Expression in Human Gastric Adenoma and Adenocarcinoma", *Virchows Arch*, 430:279-283, Springer-Verlag (1997).

Natali et al., "Clinical Significance of the $\alpha_v\beta_3$ Integrin and Intercellular Adhesion Molecule-1 Expression in Cutaneous Malignant Melanoma Lesions", *Cancer Research*, 57:1554-1560 (1997).

Natali et al., "Differential Expression of Intercellular Adhesion Molecule 1 in Primary and Metastatic Melanoma Lesions", *Cancer Research*, 50:1271-1278 (1990).

Nemunaitis, J., "Oncolytic Viruses", *Investigational New Drugs*, 17:375-386, Kluwer Academic Publishers (1999).

Newcombe et al., "Cellular receptor interactions of the C-cluster human group A coxsackieviruses", *Journal of General Virology*, 84, 3041-3050 (2003).

Newcombe et al., "Enterovirus capsid interations with decay-accelerating factor mediate lytic cell infection", *Journal of Virology*, 78(3):1431-1439 (2004).

Pulli et al., *Virology*, 212:30-38 (1995).

Randazzo et al., "Treatment of Experimental Subcutaneous Human Melanoma with a Replication-Restricted Herpes Simplex Virus Mutant", *J. Invest. Dermatol*. 108:933-937, The Society of Investigative Dermatology, Inc. (1997).

Regidor et al., "Expression of the Cell Adhesion Molecules ICAM-1 and VCAM-1 in the Cytosol of Breast Cancer Tissue, Benign Breast Tissue and Corresponding Sera", *Eur. J. Gynaecol. Oncol.*, 19(4):377-83, Abstract (1998).

Rokhlin & Cohen, "Expression of Cellular Adhesion Molecules on Human Prostate Tumor Cell Lines", *Prostate*, 26(4):205-12, Abstract (1995).

Satyamoorthy et al., "Adenovirus Infection Enhances Killing of Melanoma Cells by a Mitotoxin", *Cancer Research*, 57:1873-1876 (1997).

Schafer et al, "Correlation between ICAM-1 and depressive symptoms during adjuvant treatment of melanoma with interferon-alpha", *Brain Behav. Immuno.*, 18(6): 555-562 (2004).

Sgagias et al., "Upregulation of DF3, in Association with ICAM-1 and MHC Class II by IFN-Gamma in Short-Term Human Mammary Carcinoma Cell Cultures", Cancer Biother. Radiopharm., 11(3):177-85 (1996).

Shafren et al., *Clinical Cancer Research*, 10:53-60 (2004).

Shafren et al., *J. of Virology*, 71:9844-9848 (1997).

Shafren et al., "Coxsackievirus A21 Binds to Decay-Accelerating Factor but Requires Intercellular Adhesion Molecule 1 for Cell Entry", *Journal of Virology*, 71:4736-4743, American Society for Microbiology (1997).

Shafren et al., "Mouse Cells Expressing Human Intercellular Adhesion Molecule-1 Are Susceptible to Infection by Coxsackievirus A21", *Journal of Virology*, 71(1):785-789, American Society for Microbiology (1997).

Shafren et al "Antibody binding to individual short consensus repeats of decay-accelerating factor enhances Enterovirus cell attachment and infectivity", *The Journal of Immunology*, 160:2318-2323 (1998).

Shafren, D.R., "Viral Cell Entry Induced by Cross-Linked Decay-Accelerating Factor", *Journal of Virology*, 72(11):9407-9412, American Society for Microbiology (1998).

Staunton et al., "A Cell Adhesion Molecule, ICAM-1, is the Major Surface Receptor for Rhinoviruses", *Cell*, 56:849-853, Cell Press (1989).

Staunton et al., "Internalization of a Major Group Human Rhinovirus Does Not Require Cytoplasmic of Transmembrane Domains of ICAM-1", *The Journal of Immunology*, 148 (10):3271-3274, The American Association of Immunologists (1992).

Strong et al., "The Molecular Basis of Viral Oncolysis: Usurpation of the Ras Signaling Pathway by Reovirus", *The EMBO Journal*, 17(12):3351-3362, Oxford University Press (1998).

Suskind et al., *Proc Soc Exp Biol Med*, 94:309-318 (1957).

Taguchi et al "Circulating intercellular adhesion molecule-1 in patients with lung cancer", *Intern. Med*. vol. 36(1):14-18 (1997).

Tomassini et al., "cDNA Cloning Reveals that the Major Group Rhinovirus Receptor on HeLa Cells is Intercellular Adhesion Molecule 1", *Proc. Natl. Acad. Sci. USA*, 86:4907-4911 (1989).

Triantafillou et al "Identification of Echovirus 1 and Coxsackievirus A9 receptor molecules via a nosed flow cytometric quantification method", *Cytometry*, 43:279-289 (2001).

van den Engel, N.K. et al "Oral DNA vaccination with a plasmid encoding soluble ICAM-1 modulates cytokine expression profiles in nonobese diabetic mice", *J. Mol. Med.*, 80(5): 301-308 (2002).

Welch et al., "Characterization of a Highly Invasive and Spontaneously Metastatic Human Malignant Melanoma Cell Line", *Int. J. Cancer*, 47:227-237, Wiley-Liss, Inc. (1991).

Zhau et al., "Biomarkers Associated with Prostate Cancer Progression", *J. Cell. Biochem.*, Suppl. 19:208-216, Abstract (1994).

Gromeier et al., "Intergeneric poliovirus recombinants for the treatment of malignant glioma," *Proc. Natl. Acad. Sci.*, 97(12):6803-6808 (2000).

Holzapfel, John H., "Potentiation of the effect of oncolytic viruses," *Am. J. Obst. Gynec.*, 83:1127-1131 (1962).

Maier et al., "The adhesion receptor CD155 determines the magnitude of humoral immune responses against orally ingested antigens,", *Eur. J. Immunol.*, 37(8):2214-2225 (2007).

Pond et al., "Oncolytic effect of poliomyelitis virus on human epidermoid carcinoma (Hela tumor) heterologously transplanted to Guinea pigs,", *American Journal of Pathology, American Society for Investigative Pathology*, 45:233-249 (1964).

Sedmak et al., "Oncolytic effect of bovine enterovirus on mouse and human tumours," *Nature New Biology*, 238(79):7-9 (1972).

Taylor et al., "Viruses as an Aid to Cancer Therapy: Regression of Solid and Ascites Tumors in Rodents After Treatment with Bovine Enterovirus", *Proc. Natl. Acad. Sci.*, 68(4):836-840 (1971).

Agrez MV et al Integrin alpha v beta 6 enhances coxsackievirus B1 lytic infection of human colon cancer cells. 1997 *Virology* 239:71-77.

Alexander, C. L. et al, "The role of human melanoma cell ICAM-1 expression on lymphokine activated killer cell-mediated lysis, and the effect of retinoic acid", *Br J Cancer*, 1999, 80(10):1494-500.

Au GG et al Oncolytic Coxsackievirus A21 as a novel therapy for multiple myeloma *British Journal of Haematology*, 137:133-141, 2007.

Gromeier M et al, "Intergeneric poliovirus recombinants for the treatment of malignant glioma", *Proc. Natl Acad. Sci. USA*, Jun. 6, 2000 Lnkd-Pubmed:10841575, 97(12):6803-6808.

Holzaepfel JH. Potentiation of the effect of oncolytic viruses. *Am J Obstet Gynecol*. May 1, 1962; 83:1127-31.

Kang S-M. et al, "Significance of ICAM-1 Expression in Human Colorectal Carcinoma", *Biotherapy* (Tokyo), 1998, 12(1):157-9.

Kumegawa H., "The relationship between expression of ICAM-1 on gastric carcinoma and TIL", *The Journal of Kurume University School of Medicine*, 1994, 57(2):233-44.

Maier MK et al. "The adhesion receptor CD155 determines the magnitude of humoral immune responses against orally ingested antigens", *European Journal of Immunology* Aug. 2007, 37(8):2214-2225.

Marlin et al 1990, A soluble form of intercellular adhesion molecule-1 inhibits rhinovirus infection. *Nature* vol. 344:70-72.

Matsumori A (Ed) Cardiomyopathies and heart failure: biomolecular, infectious and immune mechanisms, 2003, Kluwer Academic Publishers, p. 247.

Nakata B. et al, "Association between Expression of Intercellular Adhesion Molecule-I and Metastasis/Invasion in Breast Cancer", *Japanese Journal of Breast Cancer*, 1998, 13(3):511-5.

Oberste, M. S. et al, "Molecular evolution of the human enteroviruses: correlation of serotype with VPI sequence and application to picornavirus classification", *J Virol*, 1999, 73(3):1941-8.

Pond A R et al., "Oncolytic effect of poliomyelitis virus on human epidermoid carcinoma (Hela tumor) heterologously transplanted to Guinea pigs", *American Journal of Pathology*, American Society for Investigative Pathology, US, Aug. 1, 1964, 45:233-249.

Pui, et al, Serum intercellular adhesion molecule-1 in childhood malignancy *Blood*, 1993, 82(3):895-898.

(56) References Cited

OTHER PUBLICATIONS

Rokhlin OA and Cohen MB Soluble forms of CD44 and CD54 (ICAM-1) cellular adhesion molecules are released by human prostatic cancer cell lines *Cancer Letters* 107 (1996) 29-35.

Sedmak G V et al, "Oncolytic effect of bovine enterovirus on mouse and human tumours", *Nature: New Biology* Jul. 5, 1972, 238(79):7-9.

Shafren DR et al Cytoplasmic interactions between decay-accelerating factor and intercellular adhesion molecule-1 are not required for coxsackievirus A21 cell infection *Journal of General Virology* (2000), 81:889-894.

Taylor M W et al., "Viruses as an aid to cancer therapy: regression of solid and ascites tumors in rodents after treatment with bovine enterovirus", *Proc. Natl Acad. Sci. USA*, Apr. 1, 1971, 68(4):836-840.

Tozawa K., "Activation of nuclera factor-x B and control of the expression of cell adhesion molecules in human prostate cancer cells", *The Journal of Japanese Urological Association*, 1996, 87(9):1082-91.

Xiao C et al., Interaction of Coxsackievirus A21 with Its Cellular Receptor, ICAM-1 *J. Virol.* Mar. 2001, 75(5):2444-2451.

* cited by examiner

METHODS FOR TREATING MALIGNANCIES USING COXSACKIEVIRUSES

CROSS REFERENCE TO RELATED APPLICATIONS

This application is a divisional application of U.S. application Ser. No. 10/148,008 filed Nov. 5, 2002, now issued as U.S. Pat. No. 7,361,354; which is a 35 USC §371 National Stage application of PCT Application No. PCT/AU00/01461 filed Nov. 27, 2000; which claims the benefit under 35 USC §119(a) to Australia Patent Application No. PQ 4256 filed Nov. 25, 1999. The disclosure of each of the prior applications is considered part of and is incorporated by reference in the disclosure of this application.

BACKGROUND OF THE INVENTION

1. Field of the Invention

The present invention relates to the killing of abnormal cells utilising a virus. There is also described a method of screening cells to ascertain whether they are susceptible to treatment with the virus, as well as pharmaceutical compositions incorporating the virus. The invention finds veterinary use as well as broad application in the human medical field.

2. Background of the Invention

Melanoma is a leading cause of morbidity in the human population. Australia has the highest rate of melanoma in the world. Melanoma is an aggressive skin cancer and is the third most common cancer in Australia for both men and women. It is predicted that one in thirty Australians have a form of melanoma resulting in the death of more than one thousand people per year in that country alone. When detected early most forms of melanoma can be effectively treated. However, the control of more advanced forms is less successful and an area of intensive research. A major goal in this area of research is the identification of molecules that are differentially expressed in benign and malignant melanocytic tumours that can be used for diagnosis and as targets for anti-cancer therapies (Kageshita T. et al; 1993).

Intercellular adhesion molecule-1 (ICAM-1), a crucial molecule in cellular inflammatory interactions, is an accepted melanoma progression antigen. Surface-expression of ICAM-1 on melanomas has been highly correlated with malignant melanoma progression (Kraus A. et al; 1997 and Morandini R. et al; 1998).

ICAM-1 is a member of the immunoglobulin (Ig) superfamily and a counter receptor for the integrin leucocyte function antigen-1 (LFA-1/CD11a) and Mac-(CD11b), and is a cellular attachment molecule for 90% of human rhinoviruses (Stuanton D. E., et al; 1989). In addition, ICAM-1 plays an important role in the pathogenesis of not only rhinovirus infection, but also in *Plasmodium falciparum* infection and in the exacerbations of asthma, chronic bronchitis and cystic fibrosis. Recently, complement regulatory proteins have been reported to be up-regulated on the surface of malignant melanomas, in particular decay-accelerating factor known as DAF (Cheung N K et al; 1998).

Viruses capable of inducing lysis of malignant cells through their replication process are known as oncolytic viruses and trials using oncolytic viruses to treat malignancies have been performed (Nemunaitis J; 1999). Most oncolytic viruses require proliferation in the same species or cell lineage. Infection of a cell by a virus involves attachment and uptake into the cell which leads to or is coincidental with uncoating of the viral capsid, and subsequently replication within the cell (Fenner F., et al. The Biology of Animal Viruses. Academic Press. New York, 1974 Second Ed.)

Oncolytic viruses assessed for capacity to kill cancer cells have included the adenovirus subtype Egypt 101 virus which showed oncolytic activity in the HeLa uterine/cervix cancer cell line, mumps virus for treatment of gastric carcinoma, uterine carcinoma and cutaneous carcinoma, Newcastle Disease Virus (NDV), influenza virus for treatment of ovarian cancer, and adenovirus for treatment of for instance, cervical carcinoma (Nemunaitis J; 1999). Other reports have indicated that adenoviruses and attenuated poliovirus recombinants may have use in the treatment of malignant glioma cells (Alemany R., et al 1999; Andreansky S. S., 1996), and that reovirus shows lytic capability in human U87 glioblastoma cells and NIH-3T3 cells with an activated Ras signalling pathway (Coffey M. C, et al, 1998; Strong J. E. et al, 1998).

In addition, a vaccinia oncolysate has been used in clinical trials to treat melanoma (Stage II) patients (Nemunaitis J., 1999), Modified, non-neurovirulent Herpes simplex viruses (HSV) have also been reported as showing promise for the treatment of brain tumours including intracranial melanoma, and subcutaneous human melanoma (Randazzo B. R., 1997), while adenovirus infection has been reported to enhance killing of melanoma cells by the plant mitotoxin, saporin (Satyamoorthy K., 1997).

The receptor on target cells recognised by adenovirus differs for different adenovirus types. That is, adenovirus subgroups A, C, D, E and F for instance recognise the CAR receptor while Adenovirus type 5 (subgroup C), Adenovirus type 2 (subgroup C) and Adenovirus type 9 (subgroup D) recognise major histocompatibility class II molecule, $\alpha_m\beta_2$ and $\alpha_v$ integrins, respectively. The CAR receptor is known to be expressed on melanoma cell lines (Hemmi S., et al, 1998). Heparan sulfate is recognised by Herpes simplex types 1 and 2 and human herpes virus 7, Adeno-associated virus type 2. The receptor for human Herpesvirus 7 is CD4 while Epstein-Barr virus recognises complement receptor Cr2 (CD21). Poliovirus type 1 and 2 recognise poliovirus receptor (Pvr) for cell adhesion while reovirus recognises sialic acid. Influenza A and B virus recognise the sialic acid N-acetyl neuraminic acid for cell adhesion. In contrast, influenza type C virus recognises the sialic acid 9-O-acetyl neuraminic acid. Vaccina virus recognises both epidermal growth factor receptor and heparan sulfate. Coxsackievirus A13, A15, A18 and A21 recognise ICAM-1 and the complement regulatory protein DAF (CD55) (see eg. Shafren D. R., et al 1997). DAF is also recognised by Enterovirus 70. See for instance Flint S J, et al (2000) Principles of Virology: molecular biology, pathogenesis and control. ASM Press, Washington.

Metastatic tumour spread is a pathological process associated with a series of adhesion/de-adhesion events coupled with regulated tissue degradation. It is known that adhesion to and migration through the extracellular matrix is essential for tumour invasion. The largest family of extracellular adhesion molecules is the integrin family (Marshall J. F. and Hart I. R., 1996) and members of the $\alpha v \beta$ group of integrins have been shown to be expressed on a variety of cell types. For instance $\alpha_v\beta_1$ is expressed on neuroblastoma, melanoma and osteosarcoma cells, $\alpha_v\beta_3$ is expressed on melanoma, glioblastoma and renal carcinoma cells, and $\alpha_v\beta_5$ is expressed on melanoma cells as is $\alpha_v\beta_8$ (Marshall J. F. and Hart I. R., 1996).

Despite progress being made in the treatment of malignancies, the treatment of cancer including melanoma presents a major challenge for research and there remains the need for alternatives to existing therapy approaches.

SUMMARY OF THE INVENTION

The present invention stems from the surprising finding of significant killing of abnormal cells can be achieved with the use of a virus and the recognition/interaction of cell expressed markers utilised by the virus for infectivity of the cells.

In one aspect there is provided a method of treating abnormal cells in a mammal comprising administering to the mammal an effective amount of a virus capable of infecting the abnormal cells whereby death of the cells is caused and which recognises at least one of a cell adhesion molecule of the immunoglobulin (Ig) superfamily and a complement regulatory protein for infectivity of the abnormal cells.

The term "abnormal cells" for the purpose of the present invention is to be taken in a broadest sense to include malignant cells, the cells of any abnormal growth and any cells having abnormal upregulated expression of at least one of the cell adhesion molecule and the complement regulatory protein relative to corresponding normal cells of the same cell type expressing their normal phenotype, whether the cells are cancer cells or not and whether the cells proliferate at an abnormal rate or not. Accordingly, the term encompasses pre-neoplastic and neoplastic cells, and non-cancer cells that may or may not ultimately develop into cancer cells. An abnormal growth may for instance be a benign or malignant tumour. Typically, the abnormal cells will be malignant cells and usually melanoma cells.

Generally, the expression of at least one of the cell adhesion molecule and the complement regulatory protein will be upregulated compared to surrounding tissue in which the abnormal cells are found.

Hence, the virus will typically preferentially infect the abnormal cells due to the greater likelihood of contacting at least one of the cell adhesion molecule and complement regulatory protein on those cells. As such the virus may be used to effectively target the abnormal cells.

In another aspect of the invention there is provided a method of treating melanoma in a mammal comprising administering to the mammal an effective amount of a virus capable of infecting melanoma cells whereby death of the cells is caused and wherein the virus recognises at least one of a cell adhesion molecule and a complement regulatory protein for infectivity of the melanoma cells.

The virus may also be used to screen cells to ascertain for instance whether the virus may be suitable for treating the patient from which the cells were obtained or whether a different treatment protocol not involving the virus may be more beneficial to the mammal. Conversely, different viruses may be screened using samples of cells taken from the patient in order to select the most appropriate virus for treating the mammal.

Accordingly, in another aspect of the invention there is provided a method of screening abnormal cells for determining whether the cells are susceptible to viral induced cell death, comprising the steps of:
(a) providing the abnormal cells;
(b) adding to the cells an effective amount of a virus which recognises at least one of a cell adhesion molecule of the immunoglobulin (Ig) superfamily and a complement regulatory protein for infectivity of the abnormal cells;
(c) incubating the abnormal cells in the presence of the virus for a period of time; and
(d) determining whether the virus has infected and caused death of at least some of the abnormal cells.

In a further aspect of the present invention there is provided a method of screening melanoma cells for determining whether the cells are susceptible to viral induced cell death, comprising the steps of:

(a) providing the melanoma cells;
(b) adding to the melanoma cells an effective amount of a virus which recognises at least one of a cell adhesion molecule and a complement regulatory protein for infectivity of the melanoma cells;
(c) incubating the melanoma cells in the presence of the virus for a period of time; and
(d) determining whether the virus has infected and caused death of at least some of the melanoma cells.

A virus may be selected for use in a method of the invention by testing whether a given virus is capable of infecting and causing the death of abnormal cells expressing at least one of the cell adhesion molecule and the complement regulatory protein. In particular, the testing may involve screening a number of different viruses by incubating each virus with a sample of the abnormal cells respectively, and determining whether the cells are killed as a result of infection.

Accordingly, in another aspect of the present invention there is provided a method of testing whether a virus is capable of infecting abnormal cells whereby death of the cells is caused and which recognises at least one of a cell adhesion molecule of the immunoglobulin (Ig) superfamily and a complement regulatory protein for infectivity of the abnormal cells.

In a further aspect of the present invention, there is provided a method of testing whether a virus is capable of infecting melanoma cells whereby death of the cells is caused and which recognises at least one of a cell adhesion molecule and a complement regulatory protein for infectivity of the melanoma cells.

In still another aspect of the invention there is provided a method of screening a virus for ability to infect and cause death of abnormal cells, comprising the steps of:
(a) selecting a virus which recognises at least one of a cell adhesion molecule of the immunoglobulin (Ig) superfamily and a complement regulatory protein for infectivity of the abnormal cells;
(b) incubating the selected said virus with a sample of the abnormal cells for a period of time; and
(c) determining whether the selected said virus causes death of at least some of the abnormal cells.

In another aspect of the present invention there is provided a method of screening a virus for ability to infect and cause death of melanoma cells, comprising the steps of:
(a) selecting a virus which recognises at least one of a cell adhesion molecule and a complement regulatory protein for infectivity of the melanoma cells;
(b) incubating the selected said virus with a sample of the melanoma cells for a period of time; and
(c) determining whether the selected said virus causes death of at least some of the melanoma cells.

The method may also comprise the step of comparing the ability of the selected virus to infect and cause the death of the cells with that of another virus subjected to steps (b) and (c) utilising another sample of the cells.

Death of the cells following infection with the virus may result from either lysis of the cells due to intracellular replication of the virus or due to the infection triggering apoptosis most likely as a result of the activation of cellular caspases.

Once lysed, the cytosolic contents of infected cells spills from the ruptured plasma membranes, and antigens capable of eliciting an immune response to the abnormal cells may be released. Hence, treatment of abnormal cells in a mammal in accordance with a method of the invention may provide a boost to the immunity of the mammal against the abnormal cells.

Accordingly, in another aspect of the invention there is provided a method of inducing an immune response in a mammal comprising infecting abnormal cells in the mammal with a virus whereby death and lysis of the cells is caused with release of antigens therefrom for generation of said immune response, wherein the virus recognises at least one of a cell adhesion molecule of the immunoglobulin (Ig) superfamily and a complement regulatory protein for infectivity of the abnormal cells.

In yet another aspect of the present invention there is provided a method of inducing an immune response in a mammal against melanoma cells, comprising infecting the melanoma cells in the mammal with a virus whereby death and lysis of the cells is caused with release of antigens therefrom for generation of said immune response, wherein the virus recognises at least one of a cell adhesion molecule and a complement regulatory protein for infectivity of the melanoma cells.

Generally, the virus will be provided in the form of a pharmaceutical composition for use in a method of the invention. As such, in a yet further aspect of the invention there is provided a pharmaceutical composition comprising a pharmaceutically acceptable carrier together with a virus capable of infecting abnormal cells whereby death of the cells is caused and which recognises at least one of a cell adhesion molecule of the immunoglobulin (Ig) superfamily and a complement regulatory protein for infectivity of the abnormal cells.

In still another aspect of the present invention there is provided a pharmaceutical composition comprising a pharmaceutically acceptable carrier together with a virus capable of infecting melanoma cells whereby death of the cells is caused and which recognises at least one of a cell adhesion molecule and a complement regulatory protein for infectivity of the melanoma cells.

In another aspect is provided the use of the pharmaceutical composition in a method of the invention.

In a further aspect of the invention there is provided the use of a virus in the manufacture of a medicament for treating malignant cells, wherein the virus is capable of infecting the abnormal cells whereby death of the cells is caused and which recognises a cell adhesion molecule of the immunoglobulin (Ig) superfamily for infectivity of said abnormal cells.

In another aspect of the present invention there is provided the use of a virus in the manufacture of a medicament for treating melanoma wherein the virus is capable of infecting melanoma cells whereby death of the cells is caused and which recognises at least one of a cell adhesion molecule and a complement regulatory protein for infectivity of the melanoma cells.

In addition, there is provided delivery means for being held against the skin of a mammal for facilitating delivery of the virus to the mamma!, and which is impregnated with a pharmaceutical composition of the invention for contact with the skin, when the delivery means is held against said skin of the mammal in use. Generally, the delivery means will be adapted to enable it to hold in position over the skin at the desired site of treatment.

Preferably, the virus will be capable of binding to or otherwise associating with both the cell adhesion molecule and the complement regulatory protein. The complement regulatory protein will usually form a complex with the cell adhesion molecule or have a close spatial association with the cell adhesion molecule, and enhance the ability of the virus to infect the abnormal cells. Preferably, the complement regulatory protein will be decay-accelerating factor (DAF).

Preferably, the cell adhesion molecule is a member of the immunoglobulin (Ig) superfamily which includes V-CAM-1 and the intercellular adhesion molecules ICAM-1, ICAM-2 and ICAM-3. Preferably, the cell adhesion molecule is ICAM-1.

Normally, the virus will be an animal RNA virus and typically, a non-enveloped RNA virus with an icosohedral capsid and a single RNA strand genome.

Preferably, the virus will be a member of the Picornaviridae family. Members of the immunoglobulin (Ig) superfamily have a plurality of extracellular domains and the virus will desirably interact with the outermost domain closest to the N-terminus of the immunoglobulin (Ig) superfamily molecule. Preferably, the virus will be from the genus *Enterovirus* and most preferably, the virus will be a Coxsackievirus. Coxsackievirus is a human enterovirus and most enteroviral infections, even with the more virulent members of the group, cause few or no clinical symptoms. CAV21 infection for instance is associated with development of common colds and infantile diarrhoea.

Hence, in another aspect of the present invention there is provided a method of treating abnormal cells in a mammal comprising administering to the mammal an effective amount of a Coxsackievirus.

In a still further aspect of the present invention there is provided a method of treating melanoma in a mammal comprising administering to the mammal an effective amount of a Coxsackievirus.

Typically, the Coxsackievirus will be a Coxsackie A-group virus, and will normally be selected from the group consisting of Coxsackieviruses serotypes 1 to 24 (CAV1-24), and most preferably from CAV13, CAV15, CAV18 and CAV21.

While the virus will usually be a common animal virus the invention is not limited thereto and a recombinant virus engineered to be capable of infecting and causing the death of the abnormal cells, or a virus that has otherwise been modified to enhance its ability to infect the cells and cause the death of the cells post infection, may be utilised. For instance, the virus may be modified to recognise additional cell adhesion molecules such as $\alpha_v\beta_3$, $\alpha_v\beta_5$ or $\alpha_v\beta_6$.

Moreover, the same virus may be administered to the mammal during different treatment courses. Preferably, however, different viruses are used for different treatment courses to avoid or lessen the potential effect of any immune response to the previous virus administered. The virus may for instance be administered topically, intratumourally or systemically to the patient.

The mammal may be any mammal suffering from a malignancy and in need of treatment. Preferably, the mammal will be a human being.

A method of the invention may be used as an adjunct to conventional cancer treatment or as a treatment in the absence of other therapeutic treatments. In particular, a method of the invention may be utilised where conventional treatment is not suitable or practical, or in the instance where excision of abnormal cells may leave scaring or disfigurement which is unacceptable to the patient, particularly the patient's face such as from their nose or lip. Alternatively, the virus may be administered to the patient prior to and/or immediately after excision of abnormal cells.

Accordingly, the instant methods provide an alternative therapeutic treatment which may be used both following diagnosis of early stage and latter stage malignancy, and which further finds application for killing cells prior to and remaining after surgery.

Using protocols as described herein the skilled addressee will be able to readily select a suitable virus for use in the methods of the invention, and determine which abnormal cells are susceptible to infection leading to the death of the cells. The abnormal cells may for instance be prostate cancer cells, breast cancer cells, stomach cancer cells, gastric carcinoma cells, colon cancer cells, colorectal cancer cells, glioma cancer cells, skin cancer cells or other malignant cells.

A method of the invention is particularly suitable for treating a malignancy of the skin or a malignancy that has spread from the skin such as melanoma.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

The invention will now hereinafter be further described with reference to a number of non-limiting preferred embodiments.

BRIEF DESCRIPTION OF THE ACCOMPANYING DRAWINGS

Figures 3, 4:
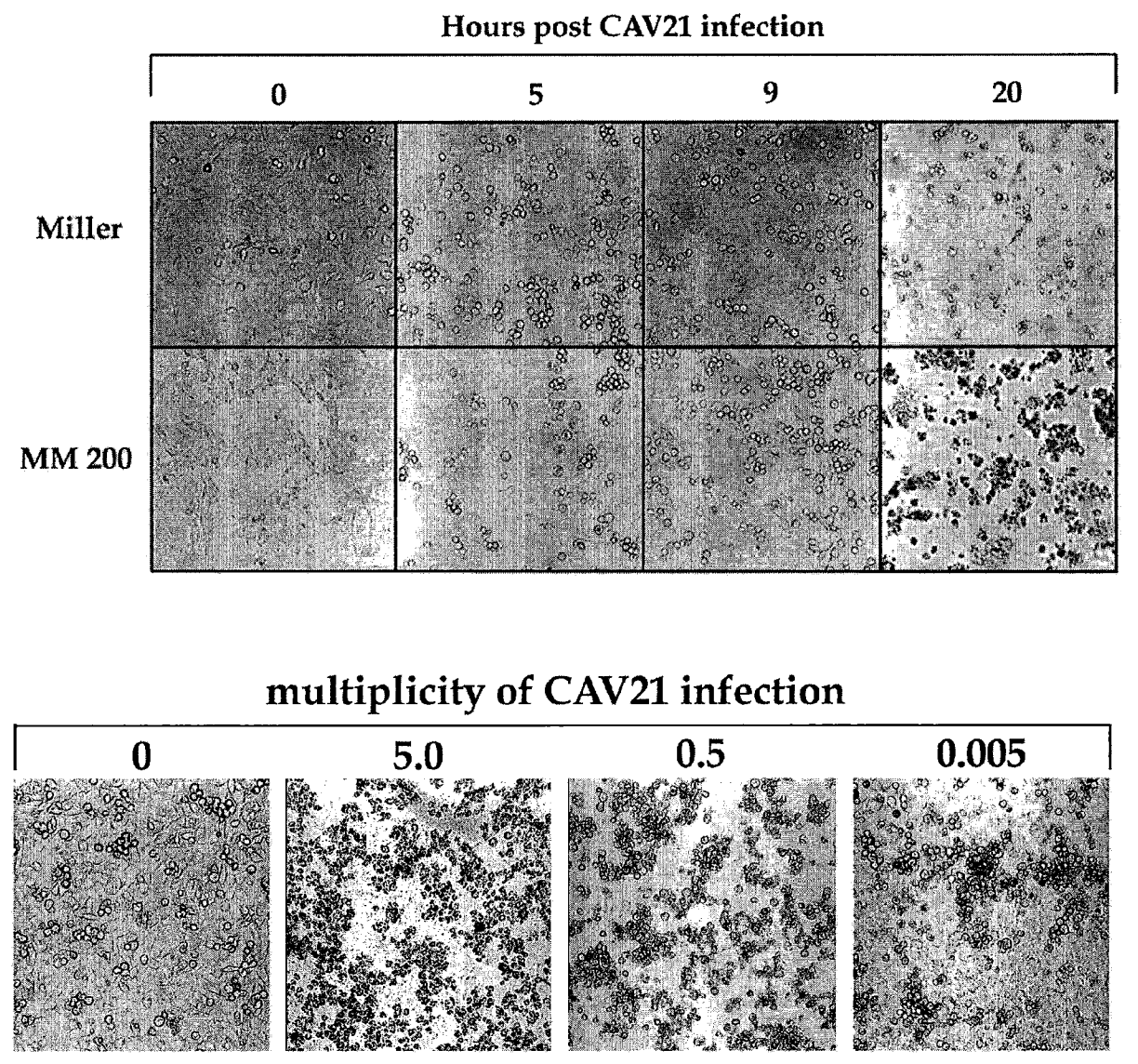
Figure 5:
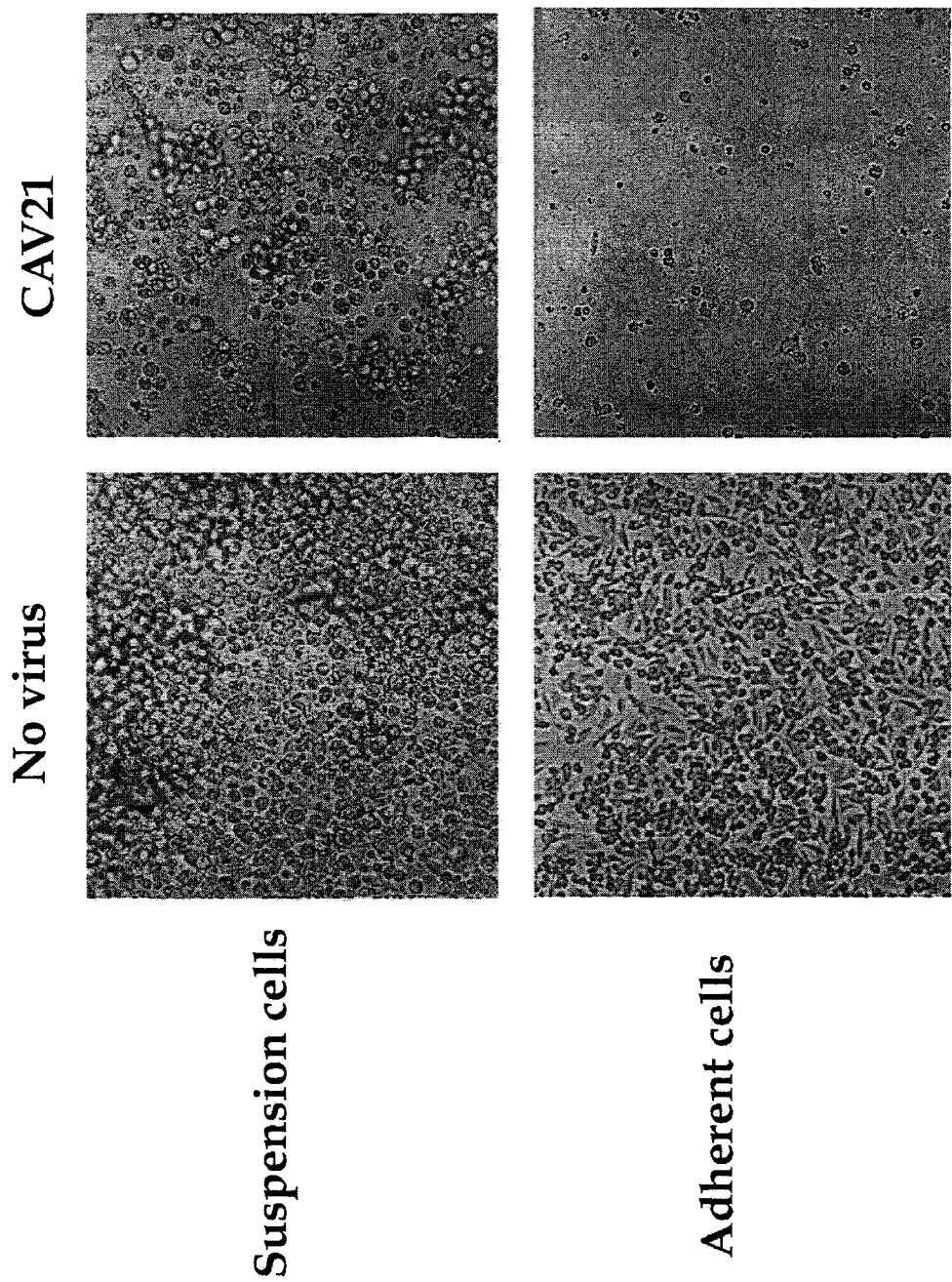
Figure 7:
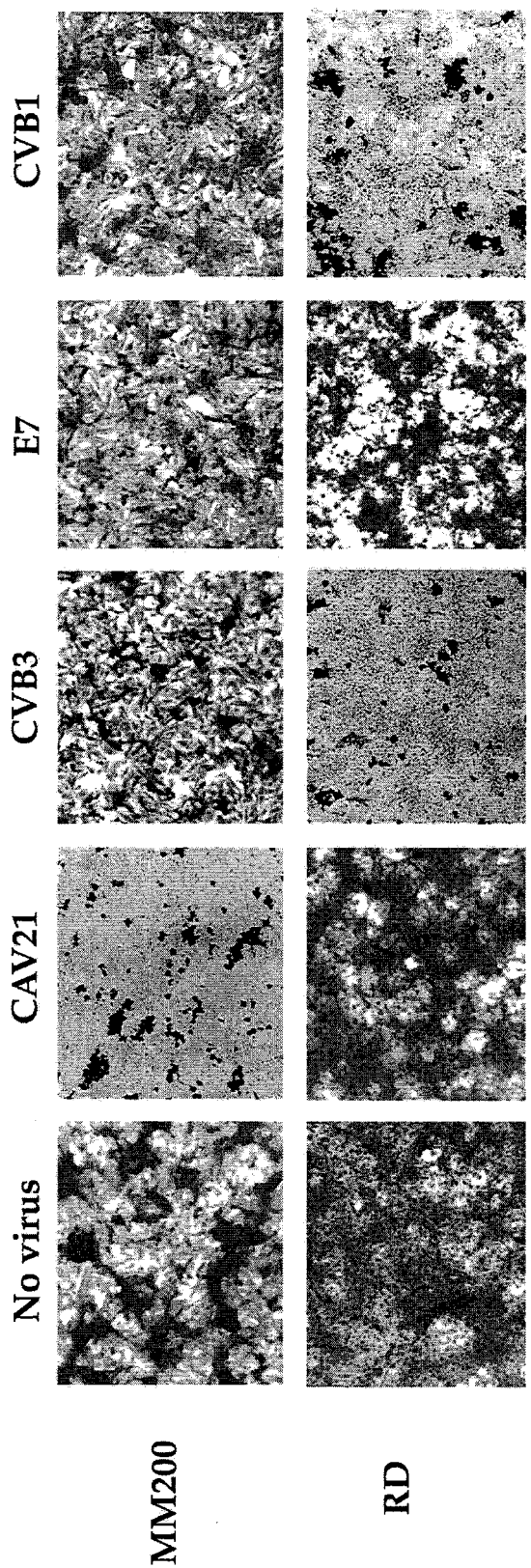
Figure 8:
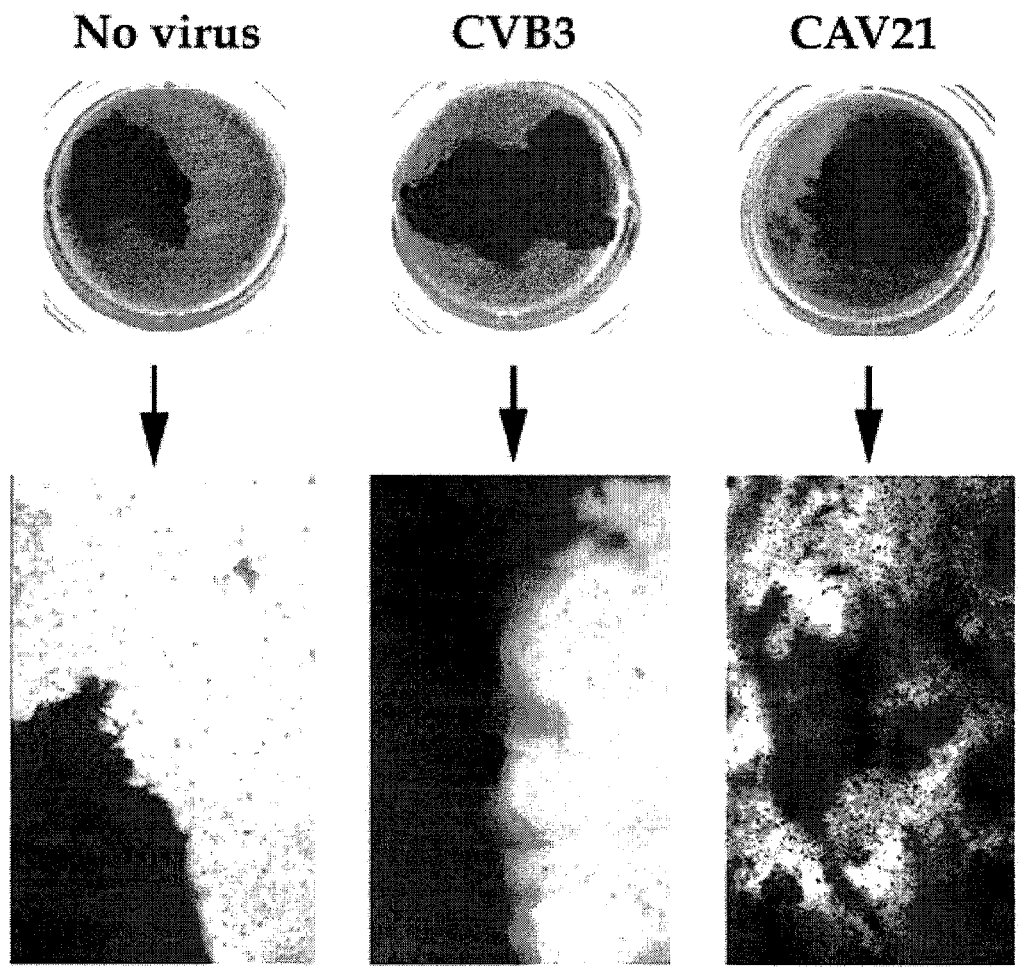
Figure 9:
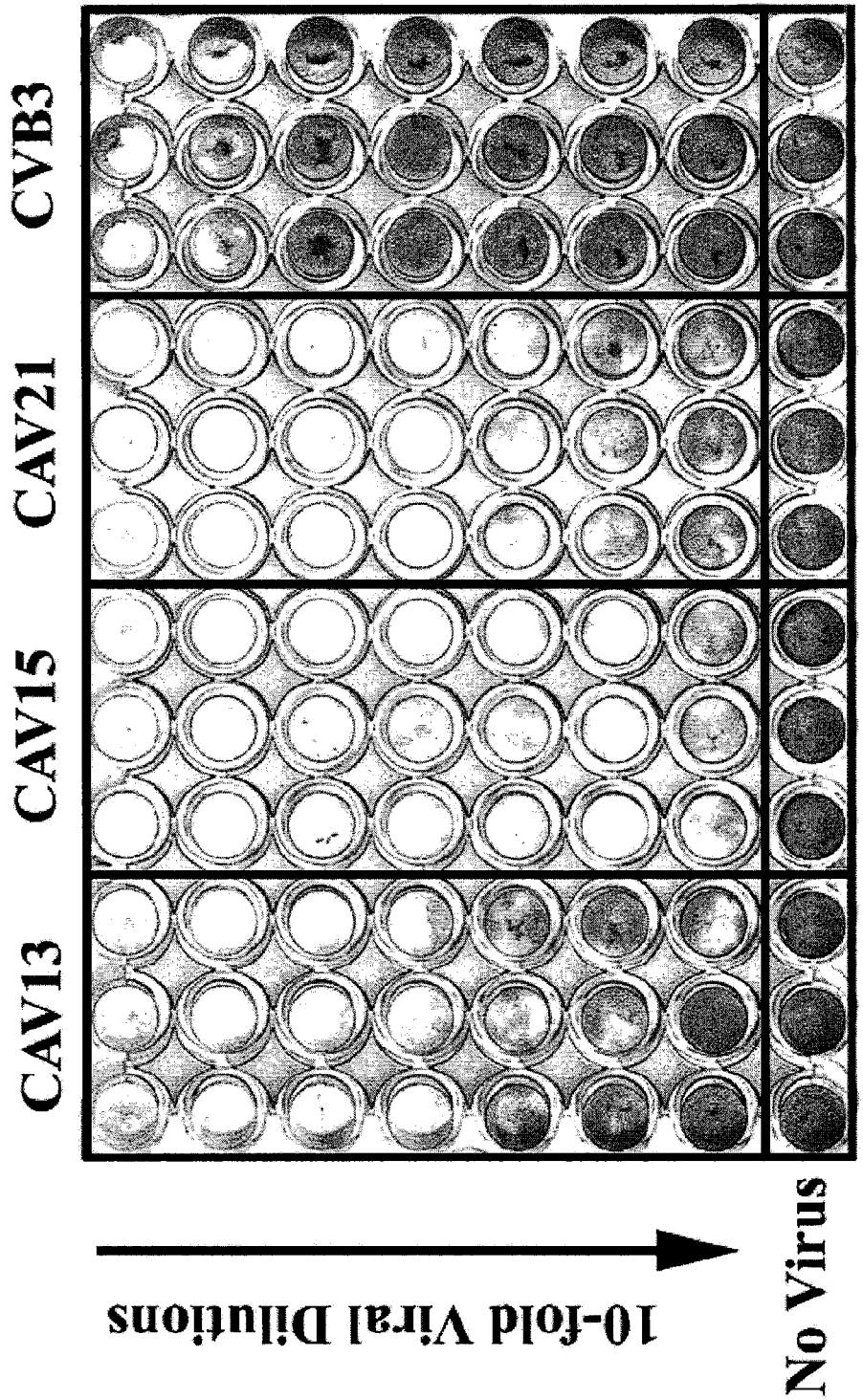
Figure 10:
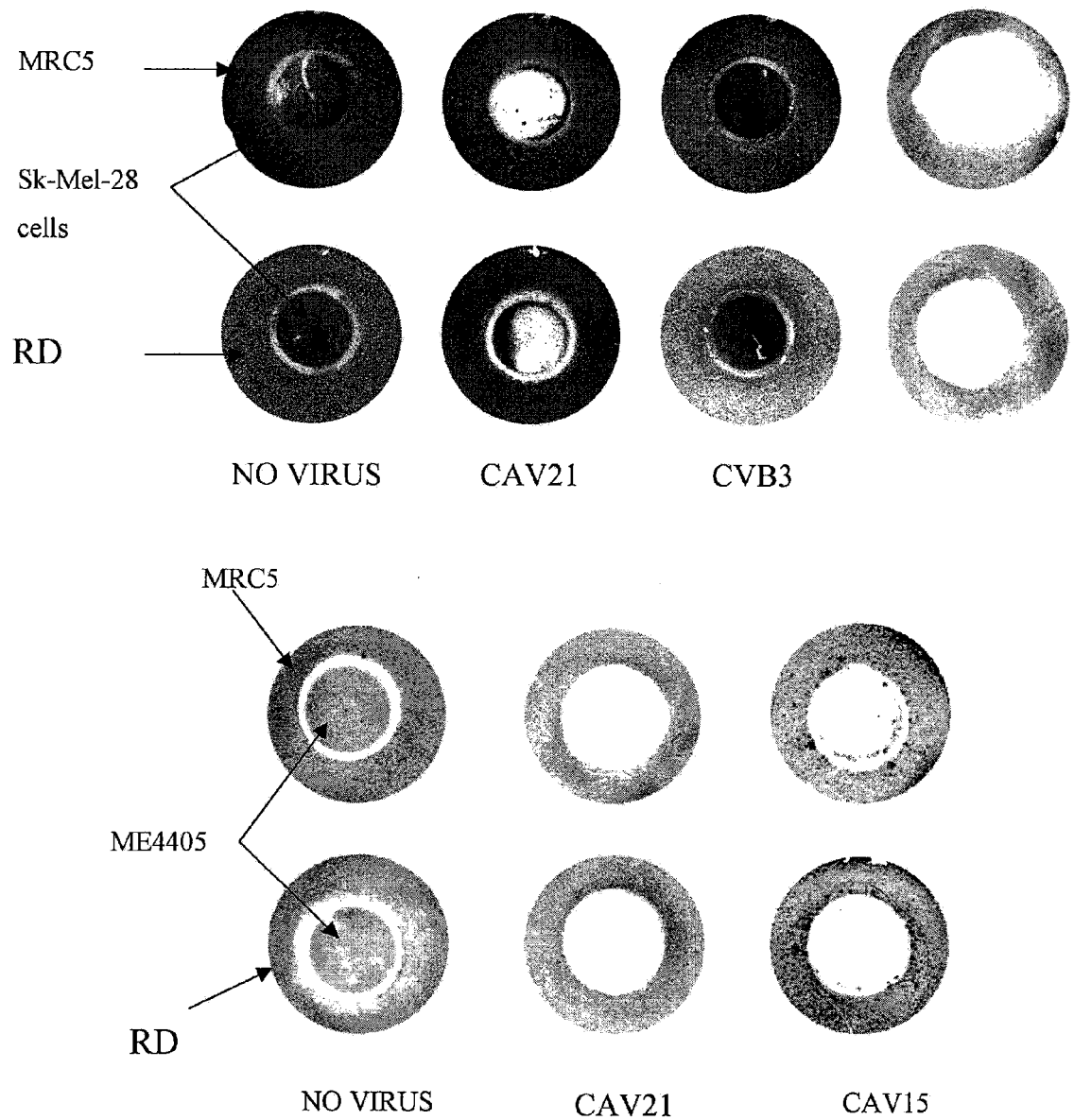
Figure 11:
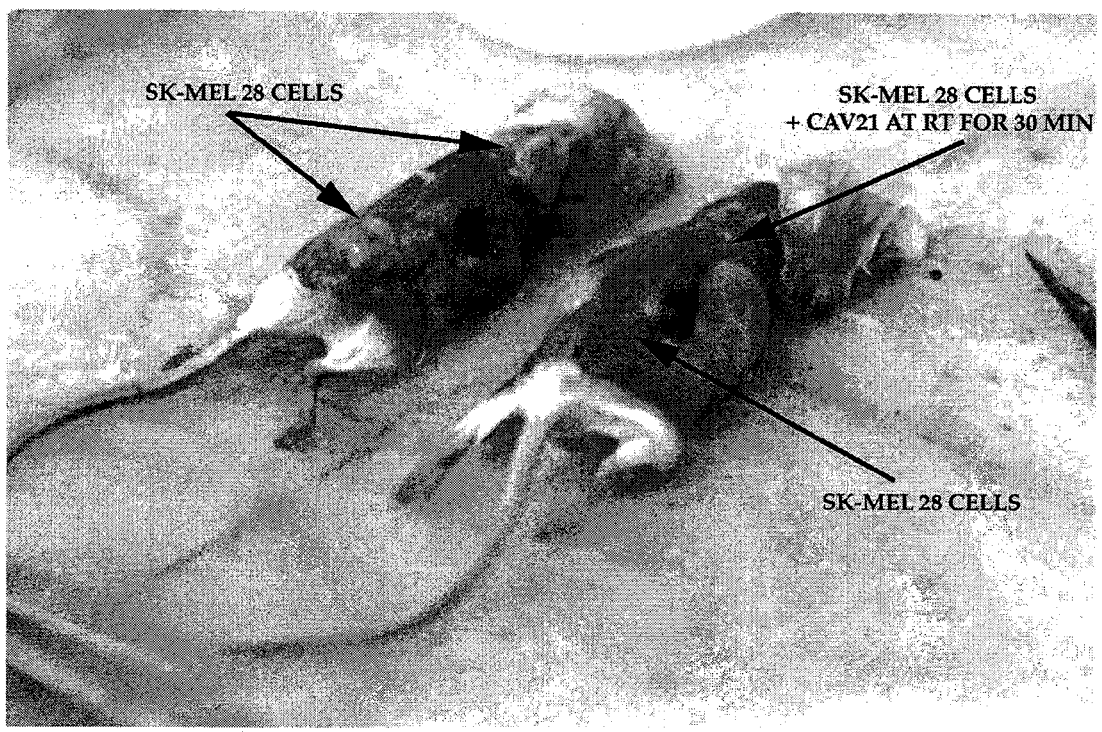
Figure 12:
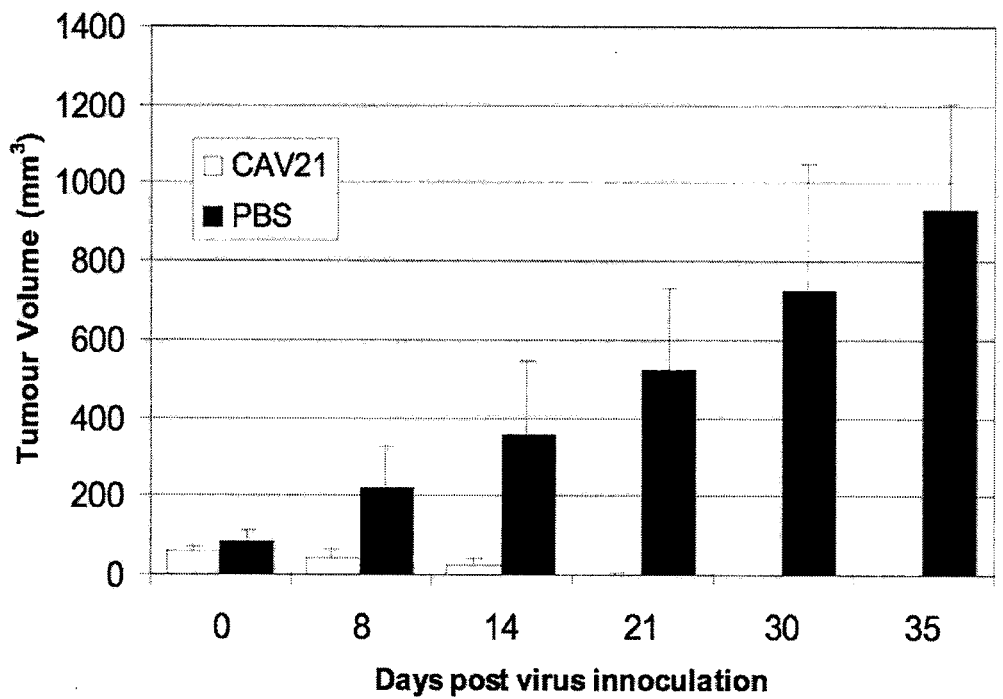
Figure 13:
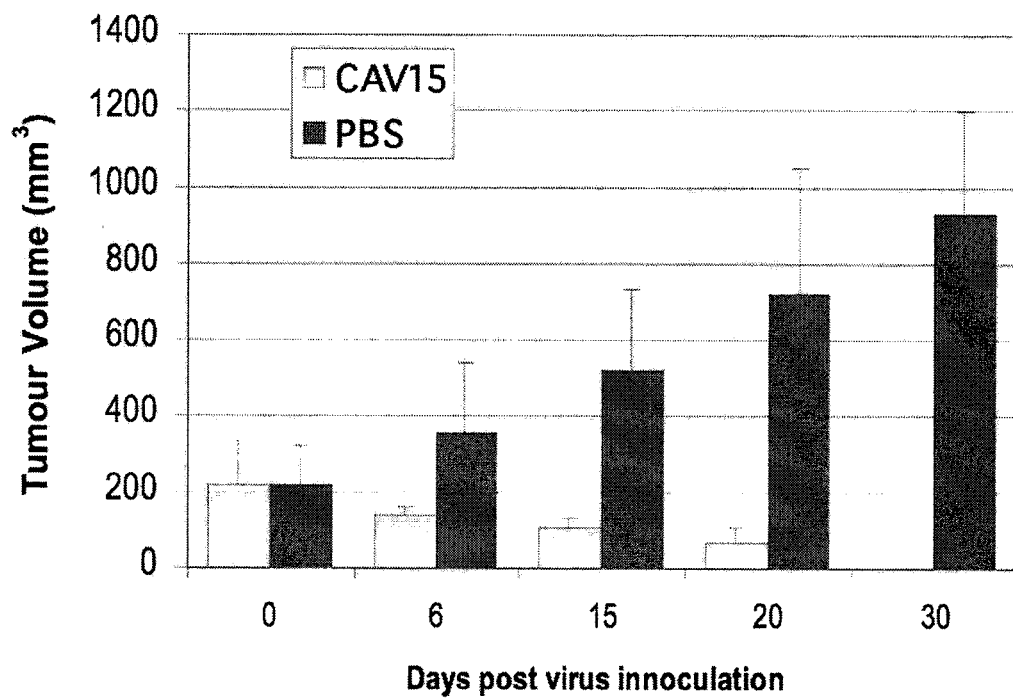
Figure 14:
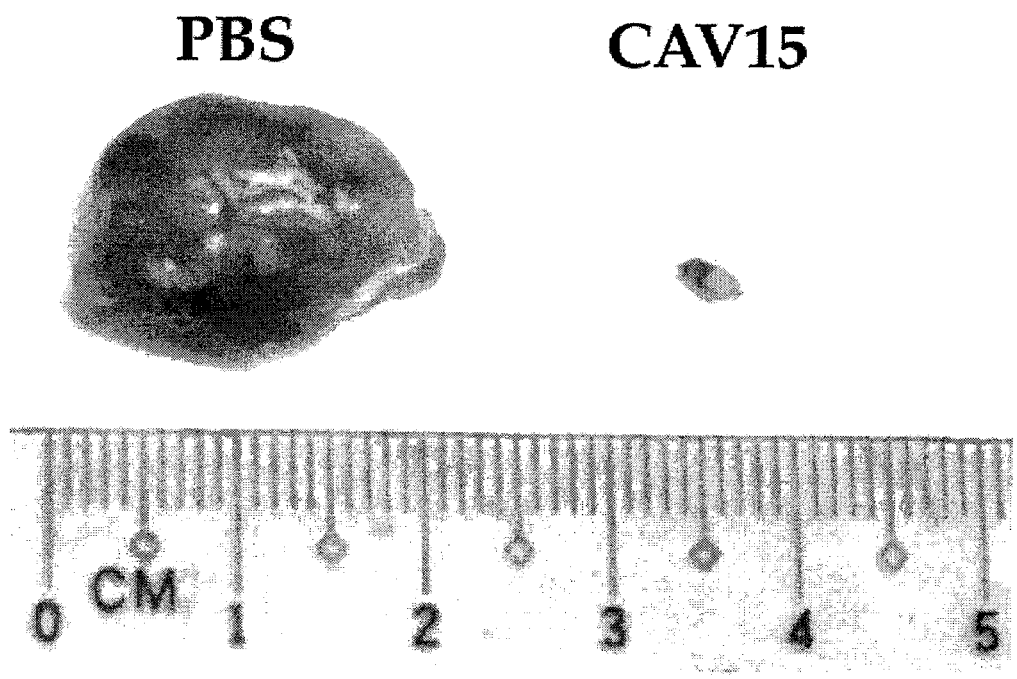
Figure 15:
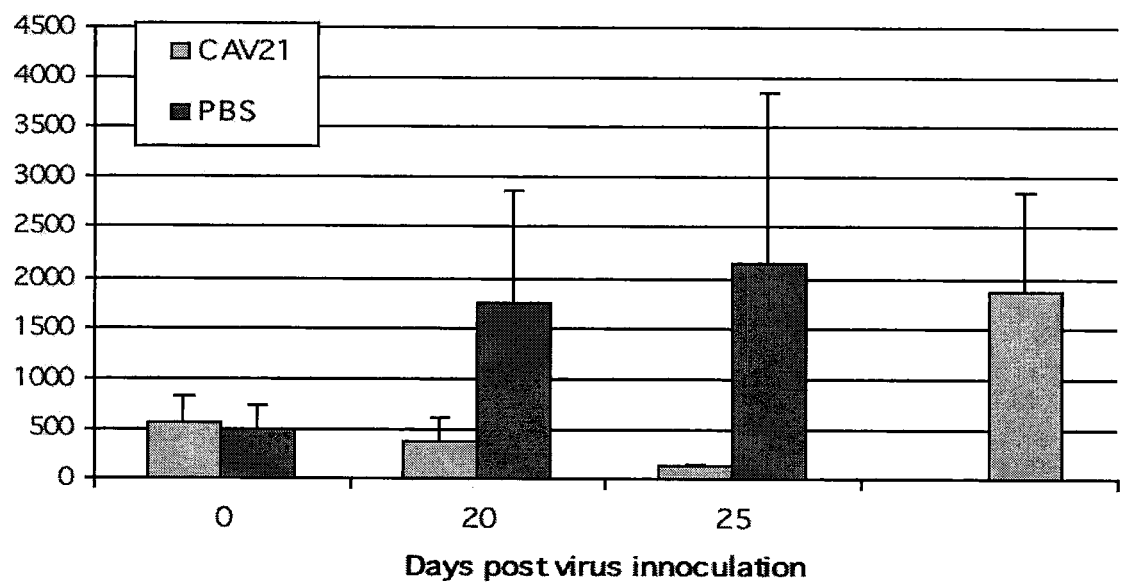

FIG. 3 indicates lytic infection of two human melanoma cells lines by Coxsackievirus A21 at different time intervals post infection;

FIG. 4 indicates lytic infection of human melanoma cells from a primary melanoma induced in a nude mouse with various doses of Coxsackievirus A21;

FIG. 5 indicates lytic infection of preparations of suspension and adherent primary malignant cells from a chest wall melanoma by Coxsackievirus A21 at 20 hours post infection;

FIG. 6 (A) indicates lytic infection of six human melanoma cell lines by Coxsackievirus A21 at twenty-three hours post infection; (B) indicates results of flow cytometric analysis of DAF (dark line) and ICAM-1 (lighter line) on the surface of human melanoma cells;

FIG. 7 indicates lytic infection of different tumour cell lines by representative human enteroviruses;

FIG. 8 indicates lytic infection of a human melanoma biopsy from lymph node by human enteroviruses Coxsackievirus A21 and B3;

FIG. 9 indicates lytic infection of prostate cancer cells by selected Coxsackievirus;

FIG. 10 shows the capacity of CAV21 and CAV15 to specifically lyrically destroy melanoma cells without infecting non-melanoma cells;

FIG. 11 indicates subcutaneous administration of CAV21 infected cells to NOD-SCID mice inhibits human melanoma tumour formation;

FIG. 12 is a graph showing results of intratumoural treatment of preformed Sk-Mel-28 melanoma with CAV21;

FIG. 13 is a graph showing results of intratumoural treatment of preformed Sk-Mel-28 melanoma with CAV 15;

FIG. 14 shows Sk-Mel-28 tumours 35 days post inoculation with PBS (left tumour) and CAV15 (right tumour); and FIG. 15 is a graph showing the effect of intratumoural treatment of preformed ME4405 melanoma with CAV21.

DETAILED DESCRIPTION OF PREFERRED EMBODIMENTS OF THE INVENTION

The following biological material was deposited under the Budapest Treaty on the dates provided below, and is available from the American Type Culture Collection (ATCC), 10801 University Blvd., Manassas, Virginia 20110-2209 USA:

Definition: Coxsackie group A virus, strain CVA13
ATCC No.: PTA-8854
Date of Deposit: Dec. 20, 2007;
Definition: Coxsackie group A virus, strain CVA15 (G9)
ATCC No.: PTA-8616
Date of Deposit: Aug. 15, 2007;
Definition: Coxsackie group A virus, strain CVA18
ATCC No.: PTA-8853
Date of Deposit: Dec. 20, 2007;
and
Definition: Coxsackie group A virus, strain CVA21 (Kuykendall)
ATCC No.: PTA-8852
Date of Deposit: Dec. 20, 2007.

To determine whether a virus is capable of infecting and causing death of cells of a tumour, a biopsy may be taken from the tumour and a preparation of cells prepared using conventional techniques prior to: (i) confirming virus receptor cell surface expression and (ii) challenging the cells with the virus and monitoring the cells for infection and cell death over a predetermined incubation period, typically about 2 days although this may vary depending on the virus used. A number of viruses may be screened in this way simultaneously utilising different aliquot's of the prepared malignant cells, the virus showing the greater degree of infectivity and cell death may then be selected for administration to the subject from whom the biopsy was taken. Similarly, different malignant cell preparations from biopsies taken from different sources may be employed in an assay using a specific virus. The biopsies may be taken from different sites of a single individual or from a number of individuals.

A virus used in a method as described herein will desirably cause few or only minor clinical symptoms in the recipient. Such viruses are readily obtainable from commercial sources well known to the skilled addressee and can be screened for their effectiveness in the instant methods in the manner described above. Desirably, the virus will normally be selected from Coxsackie A-group viruses. CAV21 is preferred and in particular CAV21 (Kuykendall) (Sickles G. M., Proc. Soc. Exp. Biol. Med. 102:742; Shafren D. et al J. Virol 1997, 71:4736; Hughes et al, J. Gen Virol. 1989, 70:2943; Schmidt, N. J., et al, Proc. Soc. Exp. Biol. Med., 1961, 107: 63. CAV21 (Kuykendall) is available from the American Type Culture Collection (ATCC) 10801 University Boulevard, Manassas, Va. 20110-2209, United States of America under Accession No. VR-850.

For the purpose of simply screening a given virus to ascertain whether it is capable of infecting and causing the death of malignant cells, malignant cell lines may be used for this purpose rather than primary malignant cells isolated from a biopsy.

Virus that recognises at least one of ICAM-1 and the complement regulatory protein DAF will typically be used. Besides being expressed on melanoma cells (Cheung N. K. et al 1998), DAF has also been shown to have upregulated expression on colonic adenocarcinoma cells in situ and on the human colonic adenocarcinoma cell line HT29. The expression of DAF has been postulated to promote resistance of the cells to complement mediated damage and so represents a possible mechanism of tumour escape (Bjørge L., et al; 1996).

Upregulated expression of ICAM-1 has been reported in a variety of malignant cell types including gastric carcinoma and adenoma cells (Nasu R., 1996; and Koyama S., 1992), prostrate cancer cells (Rokhlin O. W., and Cohen M. B., 1995), and human breast cancer cells (Sgagius M. K., 1996). Studies have also shown that V-CAM1 is expressed with ICAM-1 on breast cancer cells (Regidor P. A., et al; 1998). In addition, IC AM-1 is known to be expressed on medullary carcinoma cells (Bacuss S. S. et al; 1994), myeloma cells (Maloney D. G. et al; 1999) and thyroid carcinoma cells. ICAM-1 positive staining has also been reported in primary tumours such as papillary adenocarcinoma, and metastatic tumours from brain, liver and the adrenal gland (Fernandez-Real J. M; 1996).

Tumours occurring on the skin such as melanoma are particularly suitable candidates for treatment with the virus. In instances where melanoma has spread to lymph nodes, the lungs or other organs, the virus may be administered to those sites and/or the surrounding tissue as described above during a surgical procedure to expose such sites for treatment.

The selected virus will preferably be injected directly into a number of sites on a malignant tumour in order to maximise the area for potential infection of the tumour by the virus. Normally, tissue surrounding the tumour will be injected or otherwise treated with the virus given the possibility of malignant cells being present in the tissue. If the tumour is not detected until it is relativity advanced, surrounding tissue may be injected with the virus following surgical excision of the tumour itself.

Rather than being injected directly into a malignant tumour, the virus may be administered systemically by intravenous injection into the blood stream of the recipient at a location adjacent to the tumour site for delivery to the tumour. Similarly, the virus may be administered subcutaneously, intraperitoneally or for instance, intramuscularly if deemed appropriate. Generally, however, direct injection into the tumour is preferred given the possibility of the existence of antibodies specific for the virus and thereby the potential decreased efficacy of alternate such modes of virus delivery.

The virus may also be applied topically to tumours either alone or in combination with direct injection of the virus into the tumour. In this instance, the virus may be applied by way of delivery means for being pressed against the malignant site on the skin to be treated and which is impregnated with a suitable pharmaceutically acceptable carrier for maintaining the integrity of the virus to allow for infection of the malignant cells by the virus. The delivery means may be in the form of for instance, a patch, a pad, a wad, bandaging or the like suitable for localising the virus in the area to be treated. Typically, the delivery means will be a patch provided with an adhesive around an underside perimeter thereof for sticking the patch on the skin and thereby holding the patch in the desired position and the inoculant in contact with the patients skin.

Generally, one or more small incisions will be made into the malignancy and/or surrounding tissue to provide a site of entry for the virus into same.

The carrier medium used for inoculating the recipient with the virus may be a fluid such as physiological saline, or any other conventionally known medium deemed appropriate such as commercially available gels suitable for pharmaceutical use and for administering the virus to the site of treatment.

The inoculant will generally contain from about $1\times10^2$ to about $1\times10^{10}$ plaque forming units per ml of the inoculant. Preferably, the inoculant will contain greater than about $1\times10^5$ plaque forming units per ml of inoculant. The amount of inoculant administered to the patient may be readily determined by the attending physician or surgeon in accordance with accepted medical practice taking into account the general condition of the patient, the stage and location of the malignancy together with the overall size and distribution of the area to be treated with the virus. Typically, the patient will be treated with an initial dose of the virus and subsequently monitored for a suitable period of time before a decision is made to administer further virus to the patient pending factors such as the response of the patient to the initial administration of the virus and the degree of viral infection and malignant cell death resulting from the initial treatment.

Desirably, an individual will be treated with the virus over a period of time at predetermined intervals. The intervals may be daily or range from 24 hours up to 72 hours or more as determined appropriate in each circumstance. The same or a different virus may be administered each time to avoid or minimise the effect of any immune response to a previously administered virus, and a course of treatment may extend for one to two weeks or more as may be determined by the attending physician. Most preferably, virus to which the mammal has not previously been exposed or to which the mammal generates a relatively minor immune response as may be determined by standard techniques will be administered.

While readily available known viruses may be suitably employed in a method of the invention, a virus modified or engineered using conventional techniques may also be utilised. For instance, a virus may be modified to employ additional cell adhesion molecules as cell receptors. For example, Coxsackievirus A21 may be modified using site-directed mutagenesis so that the peptide motif "RGD" is expressed on the viral caspid surface as is the case with Coxsackievirus A9 (CAV-9). The RGD motif is recognised by all the $\alpha_v$ integrin heterodimers and this capsid modification may for instance allow the virus to bind the integrin $\alpha_v\beta_3$, a cell adhesion molecule which has been shown to be upregulated in combination with ICAM-1 on the surface of malignant melanoma lesions (Natali P. G.; 1997) leading to enhanced uptake of the virus via interaction with the integrin molecule or subsequent interaction with ICAM-1. Alternatively, the virus may be modified to recognise a selectin such as E-selectin.

The invention will now be described with reference to a number of examples described below.

EXAMPLE 1

1.1. Cell Lines

Continuous cultures of Rhabdomyosarcoma expressing ICAM-1 cells (RD-ICAM-1), HeLa-B cells, and human lung fibroblast cells (MRC5) were maintained in Dulbecco's Modified Eagle's Medium (DMEM) and 10% fetal calf serum (FCS). Two melanoma cell lines Sk-Mel-28 and ME4405 were obtained from Dr. Ralph (Department of Biochemistry and Molecular Biology, Monash University, Victoria, Australia) and Dr. Peter Hersey, Cancer Research Department, David Maddison Building Level 4, Royal Newcastle Hospital, Newcastle, New South Wales, Australia, respectively. The cell line Sk-Mel-28 is a metastatic melanoma cell line found to be resistant to chemotherapeutic drugs (56). The melanoma cell culture ME4405 was established from specimens of primary melanoma lesions (69). The two melanoma cell lines were maintained in DMEM containing 10% FCS. Rhabdomyosarcoma cells (RD) a heteroploid human embryonal cell line, and HeLa-B cells an aneuploid cell clone derived from human squamous epithelial cells, were obtained from the Entero-respiratory Laboratory, Fairfield Hospital, Melbourne, Victoria, Australia. RD cells stably transfected with cDNA encoding the immunoglobulin superfamily molecule ICAM-1 providing the RD-ICAM-1 cell line have been described elsewhere (Shafren D R, et al; 1997). MRC5 cells, derived from human lung fibroblasts were obtained from Bio-Whittaker, USA.

1.2. Viruses

Strains of CAV21 (Kuykendall strain), CAV15 (G-9) and CVB3 (Nancy) were obtained from Margery Kennett, Entero-respiratory Laboratory, Fairfield Hospital, Melbourne, Victoria, Australia.

1.3. Virus Propagation

RD-ICAM-1 cultures (80-95% confluent) were infected with $10^4$ TCID$_{50}$ (50% tissue culture infectious dose) of Coxsackievirus A strains according to standard procedures. Infected cells were incubated at 37° C. until complete cytopathic effect was observed (within 2 days). Cells were then frozen at −80° C. and thawed to release the remaining intracellular virus particles. The virus-containing medium was clarified of cellular debris by centrifugation for 5 min at 1000×g and stored as 500 µl aliquots at −80° C. CVB3 was propagated in HeLa-B cells in the same manner as described above.

1.4 Monoclonal Antibodies (MAbs)

MAb 1H4 which recognises the third SCR of DAF (24) was a gift from Dr. B. Loveland, Austin Research Institute, Melbourne, Victoria, Australia. MAb WEHI-CAM recognises the first domain of ICAM-1 (Berendt A R, et al; 1992) and was provided by Dr. A. Boyd, Walter and Eliza Hall Institute, Melbourne, Victoria, Australia.

1.5. Flow Cytometric Analysis

Cells ($1 \times 10^6$) in 100 µl aliquots were incubated with Mab IH4 or Mab WEHI-CAM diluted in DMEM containing 1% FCS on ice for 30 min. The cells were then washed with 5.0 ml of PBS, pelleted at 1,000×g for 5 min and resuspended in 100 µl of fluorescein isothiocyanate-conjugated goat anti-mouse immunoglobulin G (Silenus, Melbourne, Australia) diluted in PBS. Following incubation on ice for 30 min the cells were washed and pelleted, and resuspended in PBS for analysis with a FACStar analyser (Becton Dickinson, Sydney, Australia).

1.6. Colourimetric Infectivity Assay

The stock virus solutions of CAV21 and CAV15 were serially diluted 10-fold in DMEM containing 1% foetal calf serum (FCS). RD-ICAM-1 cell monolayers in 96-well plates were inoculated with 100 µl of serial dilutions of the viruses for 48 h at 37° C. To quantitate cell survival, monolayers were incubated with 100 µl of a crystal violet-methanol solution (5% w/v crystal violet, 10% v/v methanol, 10% v/v formaldehyde solution in PBS) and washed with distilled water. The plates were read on a multiscan enzyme-linked immunosorbent assay plate reader at a wavelength of 540 nm. Fifty percent endpoint titres were calculated (Reed L J and Muench H A; 1938) and expressed as 50% tissue culture infectious dose (TCID$_{50}$) per millilitre. A well was scored positive if absorbance was less than three standard deviations of the no-virus control. The TCID$_{50}$ for CAV21 was determined to be $2.7 \times 10^4$ units per ml while for CAV15, the TCID$_{50}$ was determined to be $1.6 \times 10^4$ units per ml.

1.7. Surface Expression of ICAM-1 and DAF

Figure 1:
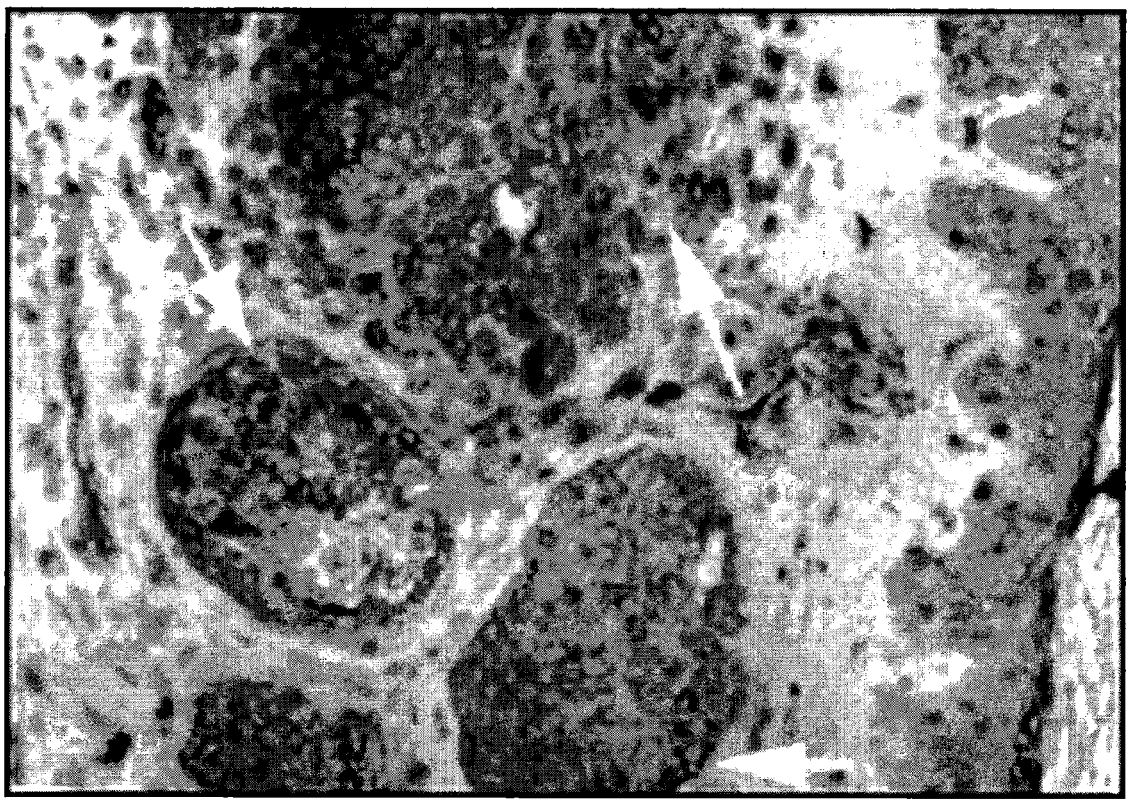
FIG. 1 shows immunoperoxidase staining of surface ICAM-1 expression on melanoma cells. ICAM-1 expression (white arrows) is indicated by dark cell staining.
Figure 2:
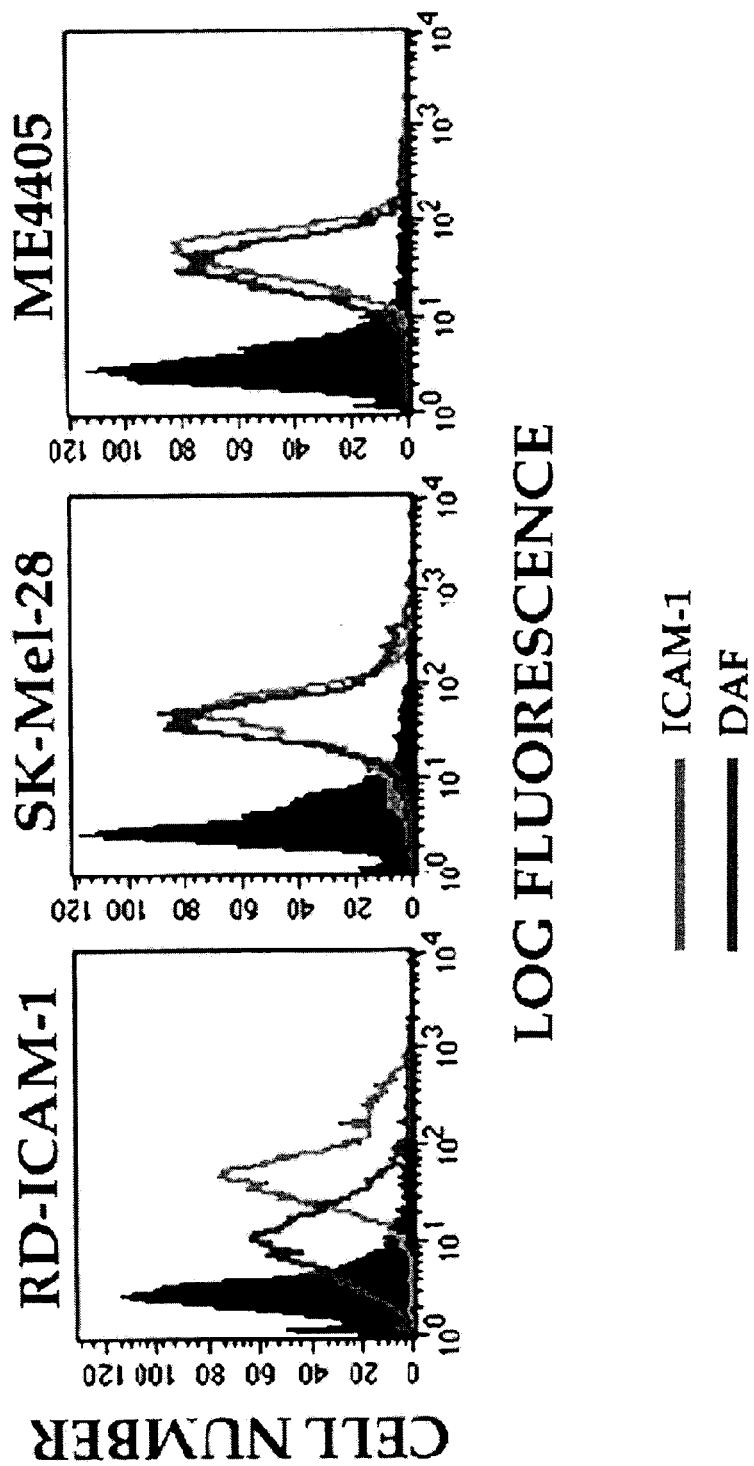
FIG. 2 shows relative levels of ICAM-1 and DAF expression by the melanoma cell lines Sk-Mel-28 and ME4405.

The relative levels of ICAM-1 and DAF expression on the surface of the melanoma cell lines SK-Mel-28 and ME4405 was determined by flow cytometric analysis. The results are shown in FIG. 2.

As can be seen, flow cytometric analysis revealed comparable high level ICAM-1 and DAF expression on the surface of the two melanoma cell lines. A further 6 melanoma cell lines derived from metastatic melanomas also expressed high levels of ICAM-1 and DAF (data not shown). The finding of high level ICAM-1 expression on all the metastatic melanoma cells tested supports several reports in the literature noting increased levels of ICAM-1 expression in vivo correlates with increased metastatic ability (Johnson J P, et al: 1988; Kageshita T, et al: 1993; Miller B E and Welch D R: 1990; Natalie P G, et al: 1997).

EXAMPLE 2

2.1. Infection of Melanoma Cell Lines by CAV21

Monolayers of two culture-adapted melanoma cell lines Miller and MM200 were infected with CAV21 prepared in Example 1 at a multiplicity of infection of 1.0 for 1 hour prior to removal of the inoculum and the cells incubated in culture medium (DMEM containing 1% foetal calf serum and penicillin streptomycin) for 24 hours at 37° C. The results shown in FIG. 3 indicate that CAV21 was able to induce significant changes in the cellular cytopathology of both cell lines as early as five hours post infection (PI) and by nine hours PI almost complete killing of all the melanoma cells.

EXAMPLE 3

3.1. Infection of Melanoma Cells from Primary Melanoma by CAV21

Cells from a primary melanoma removed from a nude mouse that had been previously subcutaneously inoculated with human melanoma cells from cell line ME 4405 using conventional methods, were highly susceptible to CAV21 infection and killing, even at a challenge rate of 0.005 CAV21 particles per melanoma cell as shown in FIG. 4.

EXAMPLE 4

4.1. Infection of Melanoma Cells Isolated From Tissue Biopsy by CAV21

Melanoma cells were isolated from fresh biopsy of a primary chest wall melanoma by the "spilling" technique and by digestion in collagen-trypsin and DNAase. Briefly, cells were released from the melanoma biopsy by macerating the biopsy with the plunger of a 10 ml syringe. The resulting melanoma cell suspension was purified on a Ficol-Hypaque (Amersham Pharmacia, Uppsala, Sweden) gradient. Contaminating fibroblasts and leucocytes were removed by mixing with Dynal beads coated with monoclonal antibodies (Mab's) to human fibroblasts (Cat#; MASS 16X, SeraLab) and to the leucocyte common antigen (CD45, Cat#17-0804-3, Amrad Biotech, Victoria, Australia).

Subsequently, $1 \times 10^6$ cells were placed into wells of a 24-well tissue culture plate and inoculated with approximately $1 \times 10^5$ plaque forming units of CAV21 prepared in Example 1. Following incubation at 37° C. for 20 hours, cells were assessed for cell death by staining with propridium iodine and microscopic analysis.

FIG. 5 shows that both adherent and suspension primary melanoma cells were efficiently killed as a result of CAV21 infection during the 20 hour incubation period.

EXAMPLE 5

5.1 Expression of ICAM-1 and DAF on Melanoma Cells Susceptible to CAV21 Infection To confirm melanoma cells are highly susceptible to infection and resultant killing by CAV21, six additional human melanoma cell lines derived from primary human melanomas were infected with CAV21 prepared in Example 1.

Figure 6A:
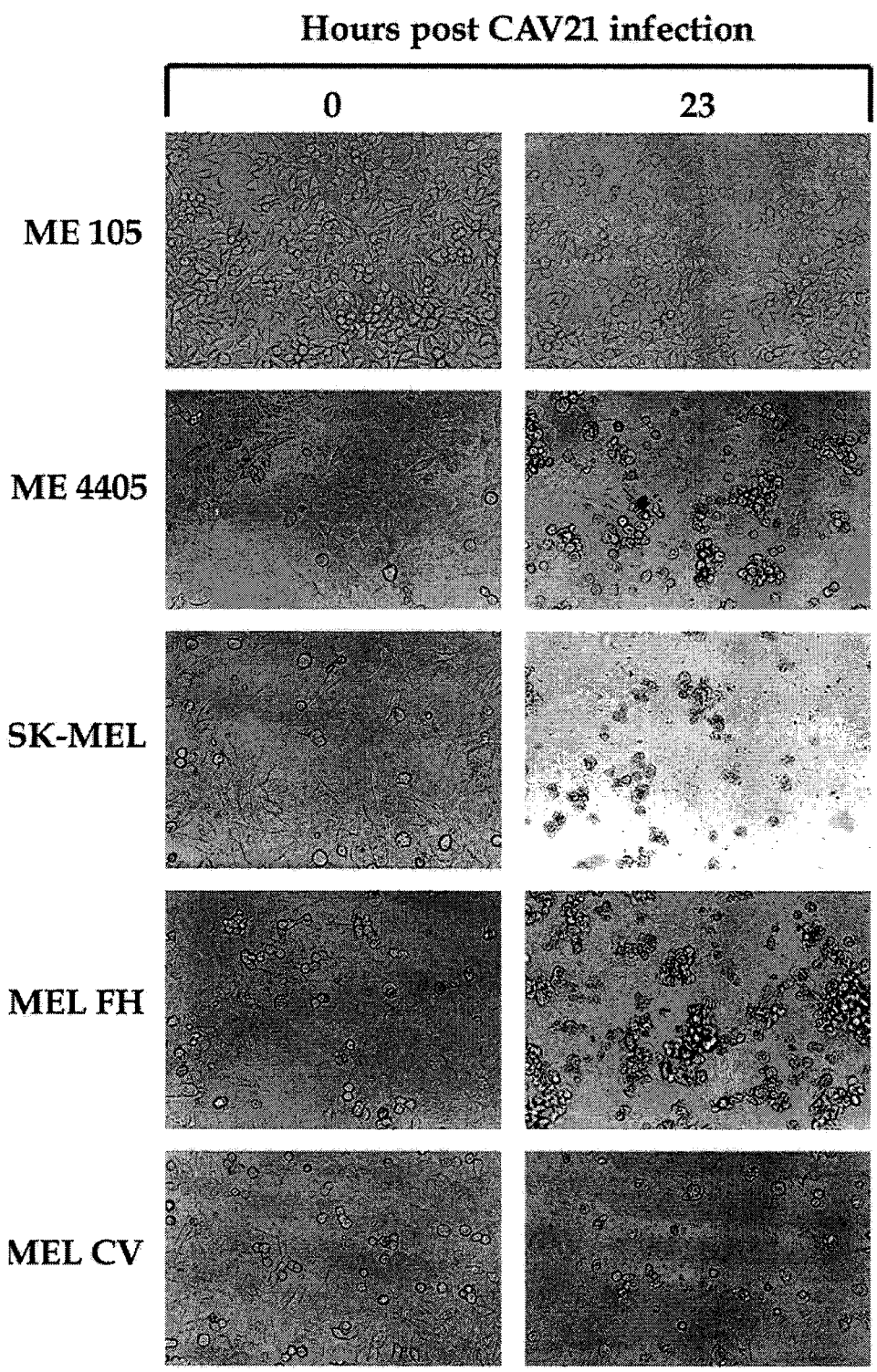
Figure 6B:
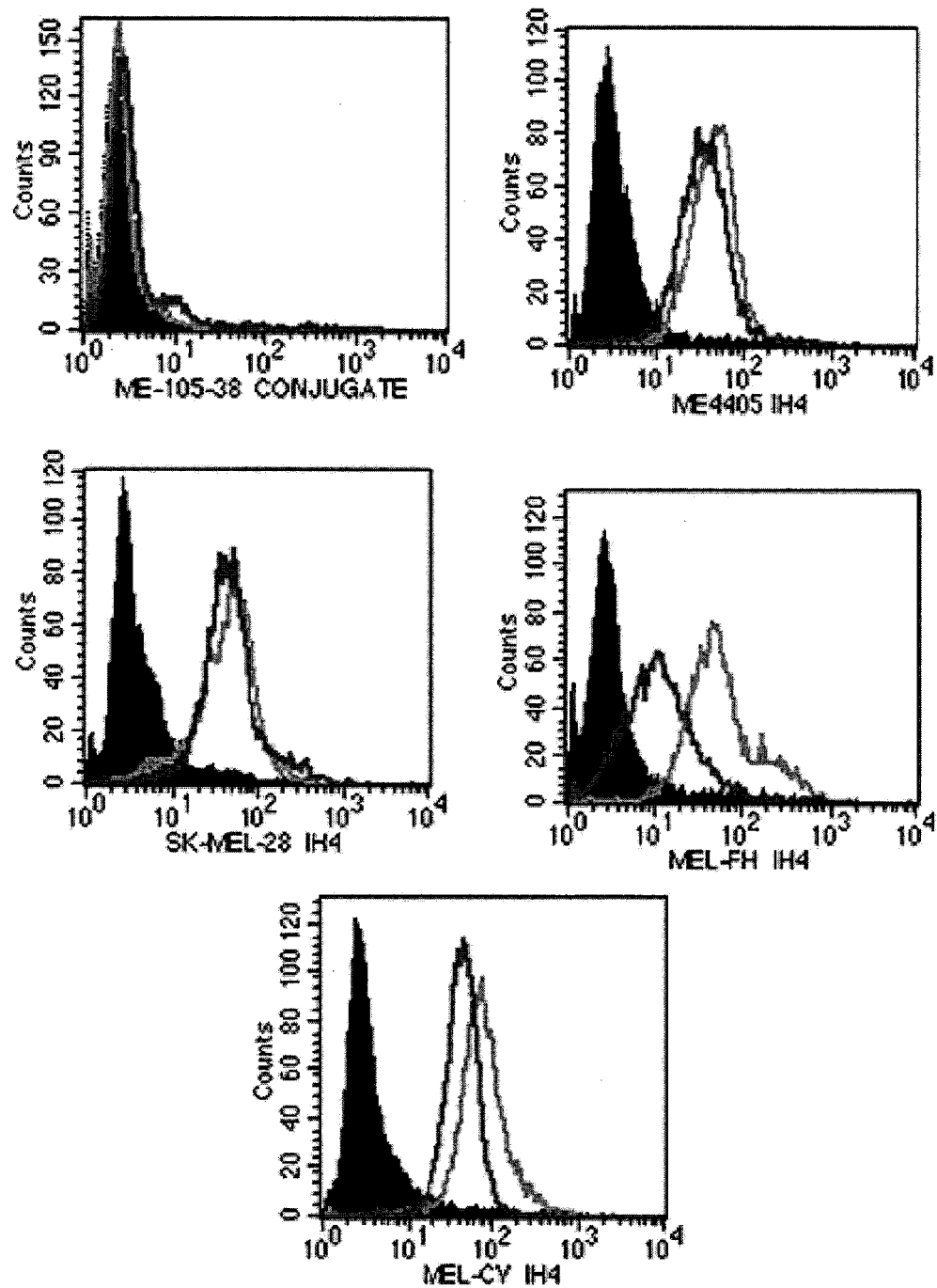

FIG. 6(A) indicates that all melanoma cell lines except one (ME 105) were killed as a result of CAV21 infection during a 23 hour incubation period.

To confirm high level expression of ICAM-1 and DAP on the surface of malignant melanoma cells, cells from each cell line were treated with the Mab IH4 and Mab WEHI-CAM. The binding of the anti-DAF and anti-ICAM-1 Mab was detected by flow cytometric analysis as described above. The fluorescence histograms shown in FIG. 6(B) confirm high level expression of DAF and ICAM-1 on the surface of all melanoma cell lines examined except the ME 105 cell line. The lack of DAF and ICAM-1 expression rendered this cell line retractile to CAV21 infection.

EXAMPLE 6

6.1 Selective Infection of Melanoma Cells Expressing ICAM-1

To highlight the selective nature of CAV21 infection of ICAM-1 expressing human melanoma cells, monolayers of melanoma cell line MM 200 were inoculated with approximately $1\times10^5$ plaque forming units of CAV21, Coxsackievirus B3 (CVB3), Echovirus type 7 (E7) or Coxsackievirus B1 (CVB1) in wells of a 24-well tissue culture plate for one hour at 37° C., respectively. The viral inoculate was subsequently removed and the cell monolayers then washed with phosphate buffered saline (PBS), and 1.0 ml of DMEM containing 1.0% foetal calf serum was added to each well and the cells incubated at 37° C. for 48 hours. To quantitate cell survival, monolayers were incubated with a crystal violet/methanol solution, washed with distilled water and microscopically examined at 100×.

FIG. 7 shows that following the 48 hour incubation period only CAV21 infected the MM 200 melanoma cells while the reverse occurred in the rhabdomyosarcoma cells (RD) where CVB 1, CVB3 and E7 infection and killing is evident. RD cells express DAF but no ICAM-1. However, when ICAM-1 is expressed on the surface of RD cells they are highly susceptible to CAV21 induced infection and killing.

EXAMPLE 7

7.1 Infection of Melanoma Biopsy With CAV21

Sections of solid human melanoma lymph node biopsies were placed in wells of a 24-well tissue culture plate and mock infected or challenged with approximately $1\times10^5$ plaque forming units of CAV21 or CVB3.

The results shown in FIG. 8 indicate that CAV21 infection resulted in severe tissue destruction around the perimeter of the melanoma biopsy treated with that virus while no detectable viral membrane destruction was observed in the mock and CVB3 infected biopsies.

EXAMPLE 8

8.1. Lytic Infection of Human Melanoma Cells by CAV21 and CAV15

To assay the oncolytic potential of CAV15 and CAV21 on human melanoma cell lines, Sk-Mel-28 and ME4405 cells were seeded into flat-bottom 96-well microtiter plates (Becton Dickenson) at $3\times10^4$ cells per well. Following incubation for 24 h at 37° C., culture medium was removed and replaced with fresh medium containing the appropriate viral serial dilution in a final volume of 100 µl. Stock viral preparations were serially diluted $10^{-1}$ through to $10^{-7}$. Following viral inoculation, the plates were incubated at 37° C. for 48 h and cell survival was detected by crystal violet staining as described above.

All three cell lines RD-ICAM-1, Sk-Mel-28 and ME4405 were found to be permissive to lytic infection by both CAV21 and CAV15. Following an incubation period of 48 h, the no virus control showed no signs of viral induced CPE while extensive cell lysis was observed across all cell cultures at a dilution of $10^{-1}$ and $10^{-2}$. At higher viral dilutions Sk-Mel-28 cells were shown to be more permissive to viral lysis compared to ME4405 and RD-ICAM-1 cell lines.

The overall oncolytic potential of CAV21 and CAV 15 was higher in the melanoma cell lines, compared to the control RD-ICAM-1 cells. While all cell types express similar levels of ICAM-1, DAF expression in RD-ICAM-1 cells is significantly lower than on melanoma cells (see FIG. 2) accounting for lower viral attachment via DAF to RD-ICAM-1 cells. DAF has previously been shown to be a low affinity sequestration molecule for many Coxsackieviruses, assisting the capture of virus particles and hence infectivity of the cells (Lea S M, et al; 1998). The presence of higher levels of DAF expression on the melanoma cell lines compared to the RD-ICAM-1 cells increases the probability of viral access to ICAM-1 receptors, thus leading to an increased level of infection and cell lysis.

8.2. Lytic Infection of Human Prostate Cancer Cells by Coxsackievirus

Cells from the human prostate cancer cell line CP3 (which expresses ICAM-1) were seeded into a flat-bottom 96-well microtitre plate (Becton Dickenson) at $3\times10^4$ cells per well and treated with serial dilutions of CAV13, CAV15, CAV21 and the Coxsackievirus B-group virus CVB3 following incubation of the cells, as described in Example 8.1 above. PC3 cells are available from the American Type Culture Collection (ATCC) Manassas, Va., USA under Accession No. CRL-1435.

As shown in FIG. 9, the PC3 cells were highly permissive to lytic infection by CAV15. Extensive lytic infection was also observed for both CAV13 and CAV21.

8.3. Selective Replication of CAV21 and CAV15 in the Human Melanoma Cell Lines Sk-Mel-28 and ME4405

The selectivity of CAV21 and CAV15 for the melanoma cell lines Sk-Mel-28 and ME4405 was studied using an in vitro specificity assay.

Sterile cell culture inserts were used to divide the wells of a standard six well plate tissue culture plate. Inside the cell culture insert, either Sk-Mel-28 cells or ME4405 cells were grown, with MRC5 or RD cells grown around the cell culture insert. Once the cells had adhered, the cell culture inserts were removed from each of the well allowing the cell culture media to evenly cover the co-culture. When the perimeters of each cell populations had fused, the co-cultures were washed twice with PBS and then inoculated with 500 µl of either PBS or stock virus ($10^5$ TCID$_{50}$) for 1 h at 37° C. Following incubation at 37° C., fresh DMEM containing 1% FCS was added to each of the wells and the plates incubated for 48 h at 37° C. in a 5% $CO_2$ atmosphere. Cell monolayers were monitored by light microscopy for signs of virus-induced CPE, prior to each well being stained with 3 ml of crystal violet solution for the detection of cell survival from viral induced lytic infection. The capacity of CAV21 and CAV15 viruses to specifically lytically destroy melanoma cells without infecting non-melanoma surrounding cells is illustrated in FIG. 10.

As can be seen, the inner cultures of melanoma cells in each well treated with CAV21 or CAV15 were totally destroyed by the viruses, but were unaffected by CVB3 virus which does not employ ICAM-1 as a receptor for cell entry. CVB3 which employs the Coxsackie- and adenovirus receptor (CAR) for cell entry (10). MRC5 cells appeared to be refractory to lytic infection by both CAV21 and CAV15. These cells are derived from a human lung fibroblast culture and only express low levels of ICAM-1 (unpublished data). The present data shows that rapid and effective lytic infection of target cells facilitated high level ICAM-1 and DAF expression. RD cells, which do not express ICAM-1, were not destroyed by either CAV21 or CAV15 infection. Furthermore, the results show little if any spread of CAV21 and CAV15 to receptor negative cells that are in direct contact with virally infected receptor-bearing cells.

EXAMPLE 9

The lytic infection of preformed melanoma tumours in vivo was evaluated by a series of animal challenge experiments using NOD-SCID mice.

9.1. Development of Melanoma Xenografts in NOD-SCID Mice

All animal work was performed under guidelines approved by The University Of Newcastle Animal Care and Ethics Committee. NOD-SCID mice were housed in pathogen-free quarters in the animal handling facility located at the David Maddison Building, Level 5, Newcastle, NSW, Australia.

Sk-Mel-28 and ME4405 cells were grown in DMEM containing 10% FCS. The cells were harvested and washed twice with DMEM, and resuspended in sterile PBS. The cell concentration of the suspension was determined with a haemocytometer and cell viability was assessed by trypan blue staining. Only cell preparations with >95% viability were used for xenotransplantation. Prior to xenotransplantation, animals were anaesthetised with intraperitoneal (i.p) injections of Rompun/Ketamine (50 mg/kg). For the monitoring of animals and measurement of tumour growth, animals were anaesthetised with 3% isofluorane.

The tumour cells were xenografted into the flank of anaesthetised 4-6 week old female NOD-SCID mice. Xenograft tumour growth was observed daily and measured with callipers at various intervals with all measurements recorded in millimetres over the course of 5 weeks. Estimates of tumour volumes were calculated using known methods (Davies C D, et al; 1997).

9.2. Subcutaneous Viral Delivery

In a preliminary experiment employing fifteen NOD-SCID mice, the local subcutaneous delivery of virus through ex vivo infected cells was assessed for inhibition of tumour growth. The mice in the control group (n=5) were injected subcutaneously with Sk-Mel-28 cells ($1 \times 10^7$) cells at individual sites in both the upper and lower flank. The CAV21 group (n=5) received an injection of $1 \times 10^7$ Sk-Mel-28 cells in the upper flank and a second injection of Sk-Mel-28 ($1 \times 10^7$) cells that had been pre-incubated with $10^4$ TCID$_{50}$ of CAV21 at room temperature for 1 hour ex vivo. The CAV15 group (n=5), was treated the same as the CAV21 group except that the second injection in the lower flank contained Sk-Mel-28 ($1 \times 10^7$) cells that had been incubated with $10^4$ TCID$_{50}$ of CAV15. Four weeks post-injection, a representative of the control group was sacrificed and shown to bear two individual tumour masses corresponding to the two injections sites of the Sk-Mel-28 ($1 \times 10^7$) cells. In contrast a representative of the CAV21 group beared no detectable tumour formation in either the uninfected cell or virally infected cell sites of injection (FIG. 11). Upon autopsy examination, all remaining members of the control group were shown to possess two distinct melanoma xenograft tumour growths, while remaining members of the CAV21 group (17 weeks post injection) exhibited no detectable tumour growth in either site of injection. Mice in the CAV15 group exhibited no tumour formation at 4 weeks post-injection.

9.3. Intratumoural Viral Delivery

Twenty NOD-SCID mice were injected with Sk-Mel 28 cells ($1 \times 10^7$) in the upper flank. When the tumour volume reached ~50-100 mm$^3$ the animals were randomly divided into groups of five and housed in separate cages. Groups of mice were injected intratumourally with 100 μl of active CAV21 or CAV15 containing $10^{3.2}$ or $10^{4.2}$ TCID$_{50}$ doses, respectively. The remaining animals received 100 μl of PBS injected directly into the xenografts. The different treatment groups were housed in individually vented cages maintained under negative pressure, ensuring that virus and other pathogens were contained within the individual cages.

A dose of $10^{3.2}$ or $10^{-4.2}$ TCID$_{50}$ of either CAV21 or CAV15 respectively, was sufficient to produce significant tumour reduction in animals bearing preformed Sk-Mel-28 tumours at 14 days post-injection. The trend of reduction of tumour burden continued for the next 14-21 days. No detectable tumours were observed at 30-35 days post-injection (see FIGS. 12 and 13). The difference observed between the CAV21 treated group and the PBS treated control group was statistically significant (P=0.0023, t test). Animals bearing Sk-Mel-28 tumours and injected with CAV21 showed no clinical signs of CAV21 illness. The capacity of CAV15 to drastically reduce melanoma tumour burden is shown in FIG. 14. At 35 days post-injection, the melanoma xenograft treated with PBS was approximately 2037 mm$^3$ while the CAV15 treated tumour was approximately 2 mm$^3$ in volume (P=0053, t test). The CAV15 treated tumour shown comprises mostly residual connective tissue.

9.4. Intratumoral Delivery of CAV21 to ME4405 Xenograft

The intratumoural delivery of CAV21 to a different melanoma (ME4405) xenograft was undertaken to further confirm the anti-tumour therapy potential of this virus. Fifteen NOD-SCID mice were injected with ME4405 cells ($5 \times 10^6$) subcutaneously in a single site on the flank. When tumour volumes had reached approximately 500 mm$^3$, the animals were randomly divided into groups of five and housed in separate cages. Five animals were injected intratumourally with 100 μl of active CAV21 containing 1032 TCID50 doses, while five mice received 100 μl of PBS injected directly into the xenografts and the remaining five mice were left untreated. As shown in FIG. 15, intratumoural administration of CAV21 was able to markedly reduce tumour development of ME4405 cells within 25 days post-injection even though the initial pre-injection tumour volume was 5-fold greater than those utilised above. The ME4405 xenografts were observed to be more aggressive than the Sk-Mel-28 tumours as assessed by significantly faster growth rates of tumours in the control groups.

The ME4405 cell line generated highly vascular aggressive tumours compared to Sk-Mel-28 tumours which grew at a slower rate and were not as vascular as the ME4405 tumours.

In contrast to mice bearing Sk-Mel-28 xenografts, when CAV21 was injected into animals with ME4405 tumours, some signs of illness were observed, the most notable being a transient weakness in both the fore and hind limbs. No positional abnormalities were observed.

9.5. Discussion of Results

This study demonstrates that CAV13, CAV15 and CAV21 have the capacity to lytically destroy malignant cell lines.

Specifically, the in vitro analysis of CAV21 and CAV15 infection of melanoma cells shows that these two viruses are able to selectively infect Sk-Mel-28 and ME4405 cell lines as a result of the expression of ICAM-1 and DAF while each of the Coxsackieviruses mentioned above were able to infect and cause the death of cells of the prostate cancer line PC3. Moreover, the intratumoural injection of CAV21 and CAV15 into xenografts of human melanoma cell lines grown in the flanks of NOD-SCID mice show that CAV21 and CAV15 possess therapeutic applications against malignant melanoma. The direct injection of either of the two viruses into pre-formed melanoma tumours suppressed tumour growth and led to significant tumour regression and in some cases complete tumour destruction compared to control animals. Furthermore, the delivery of cells infected by virus ex vivo yielded total inhibition of tumour growth and demonstrates that ex vivo CAV21 infected melanoma cells are capable of delivering sufficient virus to inhibit local tumour growth. In addition, injection of infected cells subcutaneously in a distant region to the initial tumour challenge shows that the virus can travel systemically.

The pathogenesis of CAV21 and CAV15 infections are mainly asymptomatic or manifest by no more than minor malaise. The Coe strain of CAV21 has recently been approved for live administration by the Food and Drug Administration (FDA) of the United States of America for the clinical assessment of specific anti-viral agents against CAV21 (90). The recent development of specific antiviral agents against CAV21 and CAV 15 provides the added safety precaution of drug intervention to control viral infection.

Although the present invention has been described hereinbefore with reference to a number of preferred embodiments, the skilled addressee will understand that numerous modifications and variations are possible without departing from the scope of the invention.

References Cited:

1. Kageshita T, Yoshii A, Kimura T, Kuriya N, Ono T, Tsujisaki M, Imai K and Ferrone S (1993). *Clinical relevance of ICAM-1 expression in primary lesions and serum of patients with malignant melanoma*. Cancer Res. October 15; 53(20):4927-32.

2. Kraus A, Masat L and Johnson J P (1997). *Analysis of the expression of intercellular adhesion molecule-J and MUC18 on benign and malignant melanocytic lesions using monoclonal antibodies directed against distinct epitopes and recognising denatured, non-glycosylated antigen*. Melanoma Res. August 7; Suppl 2:S75-81.

3. Morandini R, Boeynaems J M, Hedley S J, MacNeil S and Ghanem G (1998). *Modulation of ICAM-1 expression by alpha-MSH in human melanoma cells and melanoxytes*. J Cell Physiol. June; 175(3):276-82.

4. Staunton D E, Merluzzi V J, Rothlein R, Barton R, Marlin S D and Springer T A (1989). *A cell adhesion molecule, ICAM-1 is the major surface receptor for rhinoviruses*. Cell. 56:849-853.

5. Cheung N K, Walter E I, Smith-Mensah W H, Ratnoff W D, Tykocinski M L and Medof M E (1998). *Decay-accelerating factor protects human tumor cells from complement-mediated cytotoxicity in vitro*. J Clin Invest. April; 81(4): 1122-8.

6. Nemunaitis J (1999). *Oncolytic viruses*. Investigational New Drugs 17:375-386

7. Fenner F, McAuslan B R, Mims C A, Sambrook J and White D O. *The Biology of Animal Viruses*. Academic Press, New York, 1974 Second Ed.

8. Alemany R, Gomez-Manzano C, Balague C, Yung W K, Curiel D T, Kyritsis A P and Fueyo J (1999). *Gene therapy for gliomas: molecular targets, adenoviral vectors, and oncolytic adenoviruses*. Exp Cell Res. 252:1-12.

9. Andreansky S S, He B, Gillespie G Y, Soroceanu L, Markert J, Chou J, Roizman B and Whitley R J (1996). *The application of genetically engineered herpes simplex viruses to the treatment of experimental brain tumors*. Proc Natl Acad Sci USA 93:11313-8.

10. Coffey M C, Strong J E, Forsyth P A and Lee P W K (1998). *Reovirus therapy of tumours with activated Ras pathway*. Science. 282:1332-1334.

11. Strong J E, Coffey M C, Tang D, Sabinin P and Lee P W K (1998). *The molecular basis of viral oncolysis: usurpation of the Ras signalling pathway by reovirus*. 17(12):3351-3362

12. Randazzo B P, Kesari S, Gesser R M, Alsop D, Ford J C, Brown S M, Maclean A and Fraser N W (1995). *Treatment of experimental intracranial murine melanoma with a neuroattenuated herpes simplex virus 1 mutant*. Virology 211: 94-101.

13. Satyamoorthy K, Soballe P W, Scans F and Herlyn M (1997). *Adenovirus infection enhances killing of melanoma cells by a mitotoxin*. Cancer Research 57:1873-1876.

14. Hemmi S, Geertsen R, Mezzacasa A, Peter I and Dummer R (1998). *The presence of human Coxsackievirus and adenovirus receptor is associated with efficient adenovirus-mediated transgene expression in human melanoma cell cultures*. Human Gene Therapy 9:2363-2373.

15. Shafren D R, Dorahy D J, Ingham R A, Burns G F and Barry R D (1997). *Coxsackievirus A21 binds to decay-accelerating factor but requires intercellular adhesion molecule 1 for cell entry*. J. Virol. June; 71(6):4736-43.

16. Flint S J, Inquest L A W, Krug R M, Racaniello V R and Skalka A M (2000). *Principles of virology: molecular biology, pathogenesis, and control*. ASM Press, Washington.

17. Marshall J F and Hart I R (1996). *The role of αv-integrins in tumour progression and metastasis*.

18. Bjørge L, Jensen T S and Matre R (1996). *Characterisation of the complement-regulatory proteins decay-accelerating factor (DAF, CD55) and membrane cofactor protein (MCP, CD46) on a human colonic adenocarcinoma cell line*. Cancer Immunol Immunother. 42:185-192.

19. Nasu R, Mizuno M, Kiso T, Shimo K, Uesu T, Nasu J, Tomoda J, Okada H and Tsuji T (1997). *Immunohistochemical analysis of intercellular adhesion molecule-1 expression in human gastric adenoma and adenocarcinoma* Virchows Arch 430:279-283.

20. Koyama S, Ebihara T and Fukao K (1992). *Expression of intercellular adhesion molecule 1 (ICAM-1) during the development of invasion and/or metastasis of gastric carcinoma*. J. Cancer Res. Clin. Oncol. 118:609-614.

21. Rokhlin O W and Cohen M B (1995). *Expression of cellular adhesion molecules on human prostate tumor cell lines*. Prostate. April; 26(4):205-12.

22. Sgagias M K, Nieroda C, Yannelli J R, Cowan K H and Danforth Jr. D N (1996). *Upregulation of DF3, in association with ICAM-1 and MHC class II by IFN-gamma in short-term human mammary carcinoma cell cultures*. Cancer Biother Radiopharm. 11:177-85.

23. Regidor P A, Callies R, Regidor M and Schindler A E (1998). *Expression of the cell adhesion molecules ICAM-I and VCAM-I in the cytosol of breast cancer tissue, benign breast tissue and corresponding sera*. Eur J Gynaecol Oncol. 19:377-83.

24. Bacuss S S, Zelnick C R, Chin D M, Yarden Y, Kaminsky D B, Bennington J, Wen Ds Marcus J N and Page D L (1994). *Medullary carcinoma is associated with expression of intercellular adhesion molecule-1. Implication to its morphology and its clinical behaviour*. Am J Pathol. December; 145(6):1337-1148.

25. Maloney D G, Donovan K and Hamblin T J (1999). *Antibody therapy for treatment of multiple myeloma*. Seminars in Hematology. 36 (1 Suppl 3):30-33.

26. Fernandez-Real J M, Villabona C, Fernandez-Castaner M, Sagarra E, Gomez-Saez J M and Soler J (1996). *Expression of ICAM-I in distant metastatic thyroid carcinoma*. J Endocrinol Invest. March; 19(3):183-185.

27. Natalie P G, Hamby C V, Felding-Habermann B, Liang B, Nicotra M R, Di Filippo F, Giannarelli D, Temponi M, Ferrone S (1997). *Clinical significance of alpha(v) beta3 integrin and intercellular adhesion molecule-1 expression in cutaneous malignant melanoma lesions*. Cancer Res. April 15; 57(8):1554-60.

28. Reed L J and Muench H A (1938). *A simple method of estimating fifty percent endpoints*. Am J Hyg. 27:493-497.

29. Berendt A R, McDowall A, Craig A G, Bates P A, Sternberg M J E, Marsh K, Newbold C I and Hogg M (1992). *The binding site on ICAM-1 for Plasmodium falciparum-infected erythrocytes overlaps, but is distinct from the LFA-1 binding site*. Cell. 68:71-81.

30. Johnson J P, Stade B G, Hupke U, Holzmann B, Schwable W and Reithmuller G (1988). *The melanoma progression-associated antigen P3.58 is identical to the intercellular adhesion molecule ICAM-1*. Immunology. 178:275-284.

31. Miller B E and Welch D R (1990). *Intercellular adhesion molecule-1 (ICAM-1) expression by human melanoma cells; association with leukocyte aggregation and metastatic potential*. Clin. Exp. Metastasis. 8:80.

32. Lea S M, Powell R M, McKee T, Evans D J, Brown D, Stuart D I and van deer Merowe P A (1998). *Determination of the affinity and kinetic constants for the interaction between the human virus echovirus II and its cellular receptor*, CD55. J. Biol. Chem. 273:30443-60447.

33. Davies C A L, Muller H, Hagen I, Gareth M and Helton M H (1997). *Comparison of extracellular matrix in human osteosarcomas and melanomas growing as xenografts, multicellular spheroids and monolayer cultures*. Anticancer Research. 17:4317-4326.

What is claimed is:

1. A method of treating abnormal cells in a mammal, comprising administering to the mammal an effective amount of a human Enterovirus-C (HEV-C) that binds to intercellular adhesion molecule-1 (ICAM-1) for infectivity of the abnormal cells and is thereby capable of infecting the abnormal cells whereby death of the cells is caused, wherein the abnormal cells are cancer cells, and further wherein the HEV-C is administered intravenously, intratumorally, intraperitoneally or intramuscularly.

2. The method of claim 1, wherein the HEV-C binds to both ICAM-1 and decay accelerating factor (DAF) for infectivity of the abnormal cells.

3. The method of claim 1, wherein expression of ICAM-1 is upregulated on the abnormal cells relative to normal said cells expressing their normal phenotype.

4. The method of claim 1, wherein expression of ICAM-1 is upregulated on the abnormal cells relative to cells of surrounding tissue in which the abnormal cells are found.

5. The method of claim 1, wherein the HEV-C is a Coxsackievirus.

6. The method of claim 1, wherein the HEV-C is a recombinant virus.

7. The method of claim 1, wherein the abnormal cells are cells of a malignancy selected from the group consisting of a malignancy of the skin, melanoma, multiple myeloma, head and neck cancer, prostate cancer, stomach cancer, breast cancer, gastric cancer, colorectal cancer, glioma, and colon cancer.

8. The method of claim 1, wherein the HEV-C is administered by injection.

9. The method of claim 1, wherein the HEV-C is administered to the mammal in a dosage greater than about $1 \times 10^2$ plaque forming units per ml of inoculant.

10. The method of claim 9, wherein the HEV-C is administered to the mammal in a dosage of between about $1 \times 10^2$ to $1 \times 10^1$ plaque forming units per ml of the inoculant.

\* \* \* \* \*